(12) United States Patent
Vanoli et al.

(10) Patent No.: US 12,389,846 B2
(45) Date of Patent: *Aug. 19, 2025

(54) LETTUCE VARIETY 'PS 1525'

(71) Applicant: Pinnacle Seed, Inc., Carmel, CA (US)

(72) Inventors: Mike Vanoli, Carmel, CA (US); Michael Koda, Yuma, AZ (US)

(73) Assignee: PINNACLE SEED, INC., Carmel, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 17/727,631

(22) Filed: Apr. 22, 2022

(65) Prior Publication Data
US 2022/0346338 A1 Nov. 3, 2022

Related U.S. Application Data

(60) Provisional application No. 63/178,895, filed on Apr. 23, 2021.

(51) Int. Cl.
*A01H 6/14* (2018.01)
*A01H 5/12* (2018.01)

(52) U.S. Cl.
CPC ............ *A01H 6/1472* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 7,371,933 B1 | 5/2008 | Knerr | |
| 8,362,326 B2 | 1/2013 | Bellec | |
| 8,389,810 B2 | 3/2013 | Ammerlaan | |
| 8,404,937 B2 | 3/2013 | Gibson | |
| 8,476,498 B2 | 7/2013 | Peng | |
| 8,772,578 B2 | 7/2014 | Ammerlaan | |
| 9,320,250 B2 | 4/2016 | Ammerlaan | |
| 9,814,210 B2 | 11/2017 | Ammerlaan et al. | |
| 9,913,452 B2 | 3/2018 | Munoz | |
| 10,123,502 B2 | 11/2018 | Vanoli | |
| 10,631,491 B2 | 4/2020 | Vanoli | |
| 10,785,937 B1 | 9/2020 | Vanoli | |
| 11,369,069 B2 | 6/2022 | Vanoli | |
| 11,369,070 B2 | 6/2022 | Vanoli et al. | |
| 11,723,329 B2 * | 8/2023 | Vanoli .................. | A01H 6/1472 800/260 |
| 11,758,861 B2 | 9/2023 | Vanoli | |
| 2012/0278955 A1 | 11/2012 | Gibson | |
| 2012/0297496 A1 | 11/2012 | van der Laan | |
| 2013/0171323 A1 * | 7/2013 | Jansen ............... | C12N 15/8286 800/301 |
| 2014/0101794 A1 | 4/2014 | Gibson | |
| 2015/0208602 A1 | 7/2015 | Waycott | |
| 2017/0251622 A1 | 9/2017 | Sinclair et al. | |
| 2018/0249669 A1 | 9/2018 | Sinclair | |
| 2019/0230883 A1 | 8/2019 | Heintzberger et al. | |
| 2020/0288660 A1 | 9/2020 | Vanoli | |
| 2020/0375137 A1 | 12/2020 | Vanoli | |
| 2021/0084853 A1 | 3/2021 | Vanoli | |
| 2021/0400893 A1 | 12/2021 | Vanoli | |
| 2022/0264814 A1 | 8/2022 | Vanoli et al. | |
| 2022/0279747 A1 | 9/2022 | Vanoli | |
| 2023/0329174 A1 | 10/2023 | Vanoli et al. | |
| 2024/0040983 A1 | 2/2024 | Vanoli | |
| 2024/0090399 A1 | 3/2024 | Vanoli et al. | |

OTHER PUBLICATIONS

Pinnacle Seed. 2022. 'Coastal Icebergs'. Cheat Sheet. Distributed to growers on Dec. 1, 2022, 2 pages.
Pinnacle Seed. 2023. 'Desert'. Cheat Sheet. Distributed to growers on Jul. 19, 2023, 2 pages.
Grant, A. (2018). "Different Lettuce Types: Varieties of Lettuce for the Garden," Obtained from <https://www.gardeningknowhow.com/edible/vegetables/lettuce/different-lettuce-types.htm>, 7 pages.
Liu et al., (1999). "First Report of Tomato Bushy Stunt Virus Isolated from Lettuce," Plant Disease, 83(3):301, 3 pages.
Mikel, M. (2013). "Genetic composition of contemporary proprietary U.S. lettuce (*Lactuca sativa* L.) cultivars," Genet Resour Crop Evol, 60:89-96.
Nagata, R. T. (1992). "Clip and Wash Method of Emasculation for Lettuce." HortScience 27(8):907-908.
Notice of Release of iceberg lettuce breeding lines submitted by the United States Department of Agriculture and University of California, Davis dated Jun. 4, 2015 and Jul. 1, 2015, 4 pages.
Obermeier et al., (2001). "Characterization of Distinct Tombusviruses that Cause Diseases of Lettuce and Tomato in the Western United States." Phytopathology, 91(8): 797-806.
Pinnacle Seed. Jun. 2019. 'Hotshot'. Product Sell Sheet. Available online at <http://pinnacleseed.net/sell-sheets/hotshot-sell-sheet.pdf>, Obtained on Sep. 18, 2020.1 page.
Pinnacle Seed. Jun. 2019. 'Uppercut'. Product Sell Sheet. Available online at <http://pinnacleseed.net/sell-sheets/PIN-021-Uppercut-sell-sheet-R1-20200310.pdf>, Obtained on Sep. 18, 2020.1 page.
Pinnacle Seed. Oct. 2018. 'Dark Horse'. Product Sell Sheet. Available online at <http://pinnacleseed.net/sell-sheets/PIN-021-sell-sheets-dark-horse-R2-20200421.pdf>, Obtained on Sep. 18, 2020.1 page.
Pinnacle Seed. 2020. 'Latitude'. Product Fact Sheet. Available online at <https://pinnacleseed.com/wp-content/uploads/sites/14/2020/12/Pinnacle-Seed-Brochure_Iceberg-Latitude.pdf>, 1 page.
Pinnacle Seed. 2020. 'Pacific Heart'. Product Fact Sheet. Available online at <https://pinnacleseed.com/wp-content/uploads/sites/14/2020/12/Pinnacle-Seed-Brochure_Romaine_Pacific-Heart.pdf>, 1 page.
Ryder et al., (1974). "Mist depollination of lettuce flowers." HortScience, 9:584, 3 pages.
Ryder et al., (1998). "Crisphead Lettuce Resistant to Tipburn: Cultivar Tiber and Eight Breeding Lines," HortScience, 33(5):903-904.
US Plant Variety Protection Certificate No. 200700432, Issued Mar. 12, 2012, Variety Showtime, Crop Name Lettuce, Applicant Harris Moran Seed Company, 40 pages.

(Continued)

*Primary Examiner* — Shubo Zhou
*Assistant Examiner* — David R Byrnes
(74) *Attorney, Agent, or Firm* — Morrison & Foerster LLP

(57) ABSTRACT

New lettuce variety designated 'PS 1525' is described. 'PS 1525' exhibits stability and uniformity.

15 Claims, 70 Drawing Sheets
(70 of 70 Drawing Sheet(s) Filed in Color)

(56) References Cited

OTHER PUBLICATIONS

US Plant Variety Protection Certificate No. 201000303, Issued Jun. 19, 2013, Variety Caretaker, Crop Name Lettuce, Applicant Harris Moran Seed Company, 28 pages.
US Plant Variety Protection Certificate No. 201100043, Issued Mar. 21, 2018, Variety Thunderhead, Crop Name Lettuce, Applicant 3 Star Lettuce, LLC, 34 pages.
US Plant Variety Protection Certificate No. 8900281, Issued Jun. 30, 1992, Variety Raider, Crop Name Lettuce, Applicant Genecorp, Inc., 17 pages.
US Plant Variety Protection Certificate No. 9800023, Issued Nov. 26, 2020, Variety Headmaster, Crop Name Lettuce, Applicant Progeny Advanced Genetics, Inc., 35 pages.
Unpublished U.S. Appl. No. 18/336,886, filed Jun. 16, 2023, titled "Lettuce Variety 'Dark Horse'." (Copy not submitted herewith pursuant to the waiver of 37 C.F.R. § 1.98(a)(2)(iii)).

* cited by examiner

LETTUCE VARIETY 'PS 1525'

CROSS-REFERENCE TO RELATED APPLICATION

This application claims the benefit of U.S. Provisional Application No. 63/178,895, filed Apr. 23, 2021, which is hereby incorporated by reference in its entirety.

FIELD

This invention relates to the field of plant breeding. In particular, this invention relates to new lettuce, *Lactuca sativa*, varieties 'Latitude', 'Pacific Heart', and 'PS 1525'.

BACKGROUND

Lettuce is an increasingly popular crop. Worldwide lettuce consumption continues to increase. As a result of this demand, there is a continued need for new lettuce varieties. In particular, there is a need for improved lettuce varieties that are stable, high yielding, and agronomically sound.

SUMMARY

In order to meet these needs, the present invention is directed to improved lettuce varieties.

In one embodiment, the present invention is directed to lettuce, *Lactuca sativa*, seed designated as 'Latitude'. In one embodiment, the present invention is directed to a *Lactuca sativa* lettuce plant and parts isolated therefrom produced by growing 'Latitude' lettuce seed. In another embodiment, the present invention is directed to a *Lactuca sativa* plant and parts isolated therefrom having all the physiological and morphological characteristics of a *Lactuca sativa* plant produced by growing 'Latitude' lettuce seed. In still another embodiment, the present invention is directed to an $F_1$ hybrid *Lactuca sativa* lettuce seed, plants grown from the seed, and a head isolated therefrom having 'Latitude' as a parent, where 'Latitude' is grown from 'Latitude' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Latitude' lettuce plants. In another embodiment, the present invention is further directed to tissue culture of 'Latitude' lettuce plants, and to lettuce plants regenerated from the tissue culture, where the plant has all of the morphological and physiological characteristics of 'Latitude' lettuce plants.

The present invention is further directed to a method of selecting lettuce plants by: a) growing more than one 'Latitude' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Latitude' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Pacific Heart'. In one embodiment, the present invention is directed to a *Lactuca sativa* lettuce plant and parts isolated therefrom produced by growing 'Pacific Heart' lettuce seed. In another embodiment, the present invention is directed to a *Lactuca sativa* plant and parts isolated therefrom having all the physiological and morphological characteristics of a *Lactuca sativa* plant produced by growing 'Pacific Heart' lettuce seed. In still another embodiment, the present invention is directed to an $F_1$ hybrid *Lactuca sativa* lettuce seed, plants grown from the seed, and a heart isolated therefrom having 'Pacific Heart' as a parent, where 'Pacific Heart' is grown from 'Pacific Heart' lettuce seed.

Lettuce plant parts include lettuce hearts, lettuce leaves, parts of lettuce leaves, pollen, ovules, flowers, and the like. In another embodiment, the present invention is further directed to lettuce hearts, lettuce leaves, parts of lettuce leaves, flowers, pollen, and ovules isolated from 'Pacific Heart' lettuce plants. In another embodiment, the present invention is further directed to tissue culture of 'Pacific Heart' lettuce plants, and to lettuce plants regenerated from the tissue culture, where the plant has all of the morphological and physiological characteristics of 'Pacific Heart' lettuce plants.

The present invention is further directed to a method of selecting lettuce plants by: a) growing more than one 'Pacific Heart' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Pacific Heart' lettuce seed. In still another embodiment, the present invention is further directed to lettuce plants, lettuce parts from the lettuce plants (e.g., lettuce hearts), and seeds produced therefrom where the lettuce plant is isolated by the breeding method of the invention.

In one embodiment, the present invention is directed to lettuce, *Lactuca sativa*, seed designated as 'PS 1525' having ATCC Accession Number PTA-127758. In one embodiment, the present invention is directed to a *Lactuca sativa* lettuce plant and parts isolated therefrom produced by growing 'PS 1525' lettuce seed. In another embodiment, the present invention is directed to a *Lactuca sativa* plant and parts isolated therefrom having all the physiological and morphological characteristics of a *Lactuca sativa* plant produced by growing 'PS 1525' lettuce seed having ATCC Accession Number PTA-127758. In still another embodiment, the present invention is directed to an $F_1$ hybrid *Lactuca sativa* lettuce seed, plants grown from the seed, and a head isolated therefrom having 'PS 1525' as a parent, where 'PS 1525' is grown from 'PS 1525' lettuce seed having ATCC Accession Number PTA-127758.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'PS 1525' lettuce plants. In another embodiment, the present invention is further directed to tissue culture of 'PS 1525' lettuce plants, and to lettuce plants regenerated from the tissue culture, where the plant has all of the morphological and physiological characteristics of 'PS 1525' lettuce plants.

The present invention is further directed to a method of selecting lettuce plants by: a) growing more than one 'PS 1525' lettuce plant, where the plants are grown from lettuce seed having ATCC Accession Number PTA-127758; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'PS 1525' lettuce seed having ATCC Accession Number PTA-127758. In still another embodiment, the present invention is further directed to lettuce plants, lettuce parts from the lettuce plants (e.g., lettuce heads), and seeds produced therefrom where the lettuce plant is isolated by the breeding method of the invention.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows a top view of plants of lettuce variety 'Latitude'. FIG. 1B shows a bottom view of a head of lettuce variety 'Latitude'. FIG. 1C shows a cross-sectional view of a head of lettuce variety 'Latitude'. FIG. 1D shows a bottom view of heads of lettuce variety 'Latitude'. FIG. 1E shows bolting plants of lettuce variety 'Latitude'. FIG. 1F shows seedlings of lettuce variety 'Latitude'.

FIG. 2A shows a top view of a plant of lettuce variety 'Latitude' (top) and a plant of lettuce variety 'PS 1501' (bottom). FIG. 2O shows bolting plants of lettuce variety 'Tiber'. FIG. 2Q shows seedlings of lettuce variety 'Tiber.

FIG. 3A shows a top view of plants of lettuce variety 'Pacific Heart'. FIG. 3B shows a bottom view of a plant of lettuce variety 'Pacific Heart'. FIG. 3C shows a cross-sectional view of a heart of lettuce variety 'Pacific Heart'. FIG. 3D shows a bottom view of hearts of lettuce variety 'Pacific Heart'. FIG. 3E shows bolting plants of lettuce variety 'Pacific Heart'. FIG. 3F shows seedlings of lettuce variety 'Pacific Heart'.

FIG. 4A shows a top view of plants of lettuce variety 'Vicious'. FIG. 4O shows hearts of lettuce varieties 'Pacific Heart' (left) and 'Vicious' (right). FIG. 4V shows seedlings of lettuce variety 'Salvius'.

FIG. 5A shows plants of lettuce varieties 'PS 1525' (top) and 'Uppercut' (bottom).

5R shows seedlings of lettuce variety 'Uppercut'. FIG. 5S shows seedlings of lettuce variety 'Headmaster'.

DETAILED DESCRIPTION

Definitions

Figure 1A:
FIGS. 1A-1F show lettuce variety 'Latitude'.
Figure 1B:
Figure 1C:
Figure 1D:
Figure 1E:
Figure 1F:
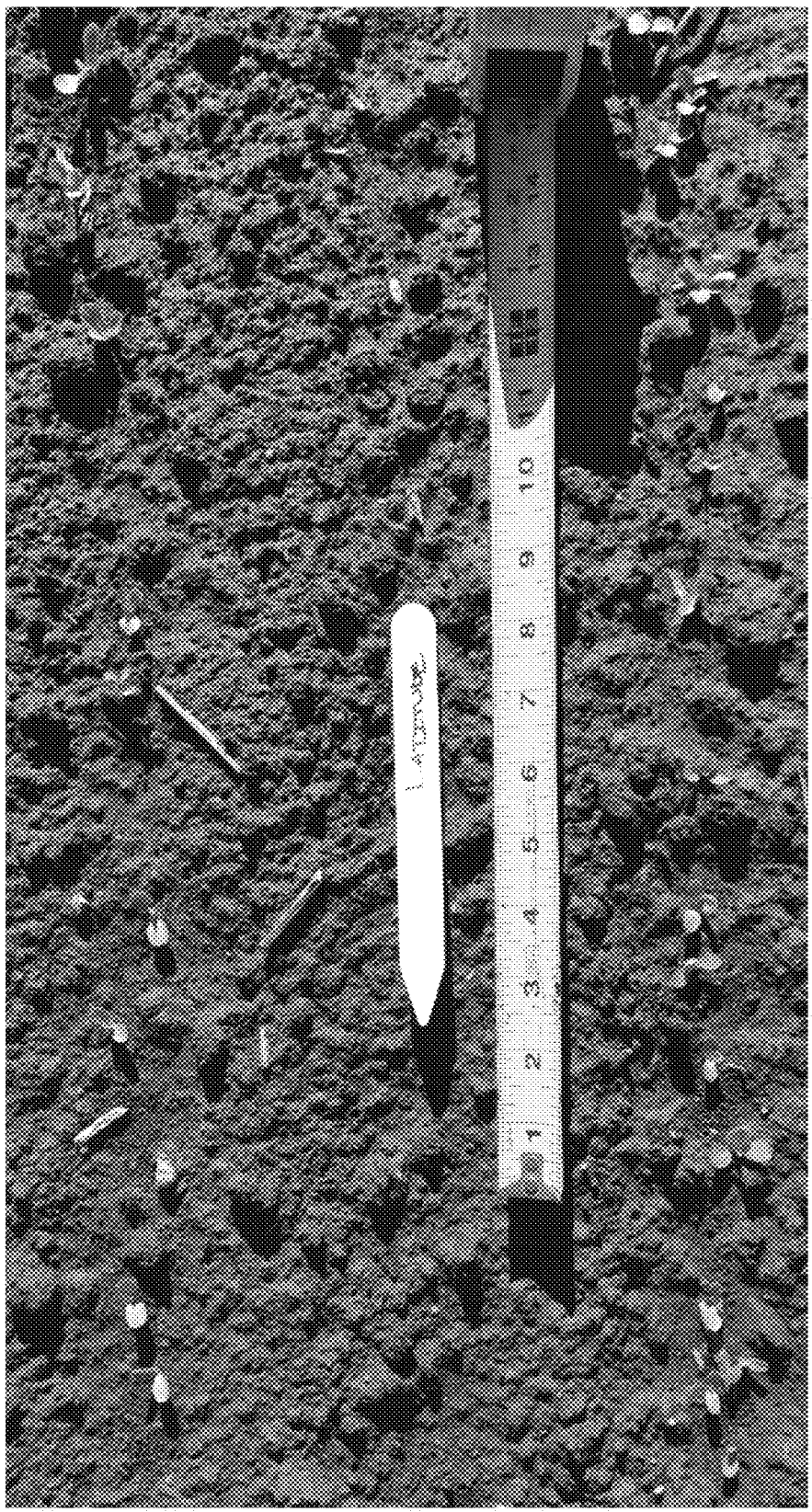

In order to more clearly understand the invention, the following definitions are provided:

Core Diameter: Core diameter is the diameter of the lettuce stem at the base of the cut head.

Core Length: Core length is the length of the vertically sliced lettuce plant as measured from the base of the cut stem to the top of the apex (growing point).

*Fusarium* Wilt: *Fusarium* wilt of lettuce is a disease caused by the fungus *Fusarium oxysporum* f. sp. *lactucae* that causes infected seedlings to wilt, and turn red or brown in color in inner tissues, and causes leaves of infected older plants to turn yellow and develop tip burn.

Head Diameter: Head diameter is the diameter of the vertically sliced iceberg lettuce plant head at its widest horizontal point, perpendicular to the stem.

Head Length: Head length is the diameter of the vertically sliced iceberg lettuce plant head as measured from the base of the cut stem to the cap leaf.

Heart: Heart is the portion in the center of romaine type lettuces where the leaf tips curve inward to cover the growing point. Cut and trimmed hearts of romaine type lettuces can be obtained by removing the frame leaves and cutting the stem off just below the base of the outermost heart leaf.

Heart Length: Heart length is the length of the vertically sliced romaine lettuce plant as measured from the base of the cut stem to the top leaf margin of the longest outermost leaf that encloses the green leaf heart.

Lettuce Mosaic Virus: A disease that can cause a stunted, deformed, or mottled pattern in young lettuce and yellow, twisted, and deformed leaves in older lettuce.

Maturity Date: Maturity refers to the stage when the plants are of full size or optimum weight, in marketable form or shape to be of commercial or economic value.

Munsell: Munsell refers to the Munsell Color Chart, which uses the Munsell color system.

*Nasonovia ribisnigri*: A lettuce aphid that colonizes the innermost leaves of the lettuce plant, contaminating areas that cannot be treated easily with insecticides.

Plant Diameter: The plant diameter is a measurement across the top of the lettuce plant at its widest point. The measurement of frame diameter is taken from the outer most leaf tip horizontally to the outer most leaf tip.

Tip burn: Means a browning of the edges or tips of lettuce leaves that is a physiological response to a lack of calcium.

*Verticillium* Wilt: *Verticillium* Wilt of lettuce is a disease caused by the fungus *Verticillium dahlia* that can cause the basal leaves that cover the outer part of the lettuce head to wilt and then collapse, leading to premature plant death and an unharvestable head.

Taking into account these definitions, the present invention is directed to seeds of the lettuce varieties 'Latitude', 'Pacific Heart', and 'PS 1525' and plants produced by growing 'Latitude', 'Pacific Heart', and/or 'PS 1525' lettuce seeds; heads or hearts isolated or harvested from the plants; one or more plants selected from a collection of 'Latitude', 'Pacific Heart', and/or 'PS 1525' plants and seeds derived or produced therefrom; and plants produced by crossing a lettuce plant with a 'Latitude', 'Pacific Heart', and/or 'PS 1525' lettuce plant and seeds derived or produced therefrom.

Objective Description of the Variety 'Latitude'

'Latitude' is an iceberg lettuce variety. This variety is distinct and unique to all other iceberg lettuce varieties due to its resistance to *Verticillium* Wilt race 1, as well as characteristics including its green color, head weight, core diameter, head diameter, time to maturity, and core length. 'Latitude' has displayed outstanding yield and shipping qualities in the months when *Verticillium* Wilt can be at its highest levels. 'Latitude' has a growing season that includes summer in West Coast regions of the United States, such as Salinas, California, and is suitable for growing in the open. FIGS. 1A-1F depict plants, heads, and seedlings of lettuce variety 'Latitude'. Lettuce variety 'Latitude' is the result of numerous generations of plant selections chosen for its high degree of resistance to *Verticillium* Wilt race 1.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Latitude'.

Lettuce variety 'Latitude' has the following morphologic and other characteristics:

Plant Type: Crisp (i.e., Iceberg)
Seed:
    Color: Black (grey brown)
    Light dormancy: Light required
    Heat dormancy: Not susceptible
Cotyledon to Fourth Leaf Stage:
    Shape of cotyledons: Broad
    Shape of fourth leaf: Round
    Fourth leaf length: 19.8 mm
    Fourth leaf width: 9.4 mm
    Fourth leaf index (length/width×10): 21.01
    Apical margin: Finely dentate
    Basal margin: Finely dentate
    Green color: Medium green
    Anthocyanin distribution: Absent
    Cupping: Slight
    Reflexing: Apical margin
Mature Leaves:
    Margin:
        Incision depth (deepest penetration of the margin): Moderate
        Indentation (finest divisions of the margin): Crenate
        Undulation of apical margin: Moderate
    Green color: Munsell 5GY 5/6 (Medium green)
    Anthocyanin distribution: Absent
    Glossiness: Moderate
    Blistering: Absent/slight
    Thickness: Intermediate
    Trichomes: Absent (smooth)
Plant:
    Weight: 681.8 g
    Spread of frame leaves: 48.7 cm
    Head diameter (market trimmed with single cap leaf): 14.2 cm
    Head shape: Spherical
    Head size class: Medium
    Head firmness: Firm
Butt:
    Shape: Flat
    Midrib: Flattened
Core:
    Diameter at base of head: 32 mm
    Ratio of head diameter/core diameter: 4.4

Height from base of head to apex: 43.3 mm
Bolting:
   Number of days from first water to seed stalk emergence under summer conditions: 74
   Bolting class: Medium
   Mature seed stalk height: 104.5 cm
   Mature seed stalk spread: 36.9 cm
   Bolter leaves: Straight
   Margin: Entire
   Bolter habit:
      Terminal inflorescence: Absent
      Lateral shoots: Present
      Basal side shoots: Absent
Disease Resistance:
   Lettuce Big-Vein Virus (LBVV): Susceptible
   Lettuce Mosaic Virus (LMV) strain Ls-1: Susceptible
   Powdery Mildew: Susceptible
   Corky Root Rot: Susceptible
   Downy Mildew (*Bremia lactucae*) (B1): Susceptible
   *Verticillium* Wilt (*Verticillium* dahlia) Race 1: Resistant
Pest Resistance:
   *Nasonovia ribisnigri* biotype 0 (Nr: 0): Susceptible
Stress Resistance:
   Tipburn: Moderately resistant
   Heat: Susceptible
   Cold: Susceptible
   Pink rib: Susceptible
   Rusty brown discoloration: Susceptible
   Internal rib necrosis: Susceptible
Comparisons to Other Lettuce Variety Table 1 below compares characteristics of lettuce variety 'Latitude' with the lettuce variety 'Tiber' (unpatented; released as PI 635075). Column 1 lists the characteristics, column 2 shows the characteristics for lettuce variety 'Latitude', and column 3 shows the characteristics for lettuce variety 'Tiber'.

TABLE 1

| Characteristic | 'Latitude' | 'Tiber' |
| --- | --- | --- |
| Green color of mature leaves | Munsell 5GY 5/6 | Munsell 5GY 5/8 |
| Head diameter | 14.2 cm | 13.7 cm |
| Head weight | 681.8 g | 611 g |
| Spread of frame leaves | 48.7 cm | 49.8 cm |
| Core diameter at base of head | 32 mm | 30.6 mm |
| Core height from base of head to apex | 43.3 mm | 44.2 mm |
| Mature seed stalk height | 104.5 cm | 105.9 cm |
| Mature seed stalk spread | 36.9 cm | 36.1 cm |

Table 2 below compares characteristics of lettuce variety 'Latitude' with the lettuce variety 'PS 1501' (unpatented; released as PI 673092). Column 1 lists the characteristics, column 2 shows the characteristics for lettuce variety 'Latitude', and column 3 shows the characteristics for lettuce variety 'PS 1501'.

TABLE 2

| Characteristic | 'Latitude' | 'PS 1501' |
| --- | --- | --- |
| Head diameter | 14.2 cm | 14.3 cm |
| Head weight | 681.8 g | 653.4 g |
| Spread of frame leaves | 48.7 cm | 49.5 cm |
| Core diameter at base of head | 32 mm | 31.1 mm |
| Core height from base of head to apex | 43.3 mm | 42 mm |
| Mature seed stalk height | 104.5 cm | 98.75 cm |
| Mature seed stalk spread | 36.9 cm | 34.8 cm |

Tables 3A-3C below show results of a first trial that compares the head weight, head diameter, core length, core diameter, and frame diameter of 20 plants of the lettuce variety 'Latitude' (Table 3A) with those of 20 plants of lettuce variety 'PS 1501' (Table 3B; unpatented; released as PI 673092) and 20 plants of lettuce variety 'Tiber' (Table 3C; unpatented; released as PI 635075). The head weights shown are total head weights.

TABLE 3A

| | 'Latitude' | | | | |
| --- | --- | --- | --- | --- | --- |
| | Head Wt. | Head Diameter | Core Length | Core Diameter | Frame Diameter |
| Max | 850 g | 164 mm | 61 mm | 35 mm | 50.2 cm |
| Min | 535 g | 122 mm | 47 mm | 28 mm | 41.6 cm |
| Average | 686.75 g | 137.2 mm | 55.15 mm | 31.75 mm | 46.025 cm |
| Std. Dev. | 95.14 | 10.30 | 3.30 | 1.92 | 2.46 |

TABLE 3B

| | 'PS 1501' | | | | |
| --- | --- | --- | --- | --- | --- |
| | Head Wt. | Head Diameter | Core Length | Core Diameter | Frame Diameter |
| Max | 985 g | 172 mm | 75 mm | 34 mm | 53.8 cm |
| Min | 445 g | 118 mm | 42 mm | 28 mm | 46.5 cm |
| Average | 740.25 g | 141.95 mm | 54.85 mm | 31.25 mm | 50.44 cm |
| Std. Dev. | 167.01 | 14.51 | 9.40 | 1.77 | 2.11 |

TABLE 3C

| | 'Tiber' | | | | |
|---|---|---|---|---|---|
| | Head Wt. | Head Diameter | Core Length | Core Diameter | Frame Diameter |
| Max | 770 g | 155 mm | 81 mm | 34 mm | 56.1 cm |
| Min | 490 g | 114 mm | 44 mm | 26 mm | 47.3 cm |
| Average | 619.5 g | 131.55 mm | 60.5 mm | 30.1 mm | 50.015 cm |
| Std. Dev. | 83.73 | 9.64 | 9.97 | 2.25 | 2.57 |

Tables 4A-4C below show results of a second trial that compares the head weight, head diameter, core length, core diameter, and frame diameter of 20 plants of the lettuce variety 'Latitude' (Table 4A) with those of 20 plants of lettuce variety 'PS 1501' (Table 4B; unpatented; released as PI 673092) and 20 plants of lettuce variety 'Tiber' (Table 4C; unpatented; released as PI 635075). The head weights shown are total head weights.

TABLE 4A

| | 'Latitude' | | | | |
|---|---|---|---|---|---|
| | Head Wt. | Head Diameter | Core Length | Core Diameter | Frame Diameter |
| Max | 885 g | 165 mm | 60 mm | 40 mm | 58.2 cm |
| Min | 510 g | 130 mm | 21 mm | 31 mm | 48.5 cm |
| Average | 744.75 g | 144.6 mm | 38.4 mm | 34.95 mm | 52.31 cm |
| Std. Dev. | 109.60 | 10.86 | 10.45 | 2.54 | 2.74 |

TABLE 4B

| | 'PS 1501' | | | | |
|---|---|---|---|---|---|
| | Head Wt. | Head Diameter | Core Length | Core Diameter | Frame Diameter |
| Max | 845 g | 160 mm | 62 mm | 36 mm | 54.3 cm |
| Min | 490 g | 125 mm | 18 mm | 28 mm | 48.3 cm |
| Average | 643.45 g | 140.3 mm | 40.65 mm | 32.95 mm | 51.775 cm |
| Std. Dev. | 114.38 | 10.50 | 11.78 | 2.44 | 1.80 |

TABLE 4C

| | 'Tiber' | | | | |
|---|---|---|---|---|---|
| | Head Wt. | Head Diameter | Core Length | Core Diameter | Frame Diameter |
| Max | 960 g | 156 mm | 73 mm | 37 mm | 54.3 cm |
| Min | 379 g | 115 mm | 24 mm | 26 mm | 46.4 cm |
| Average | 668.65 g | 138.85 mm | 38.4 mm | 31.7 mm | 50.46 cm |
| Std. Dev. | 188.48 | 10.99 | 11.84 | 3.15 | 2.57 |

Tables 5A-5C below show results of a third trial that compares the head weight, head diameter, core length, core diameter, and frame diameter of 20 plants of the lettuce variety 'Latitude' (Table 5A) with those of 20 plants of lettuce variety 'PS 1501' (Table 5B; unpatented; released as PI 673092) and 20 plants of lettuce variety 'Tiber' (Table 5C; unpatented; released as PI 635075). The head weights shown are total head weights.

TABLE 5A

| | 'Latitude' | | | | |
|---|---|---|---|---|---|
| | Head Wt. | Head Diameter | Core Length | Core Diameter | Frame Diameter |
| Max | 660 g | 141 mm | 31 mm | 33 mm | 50.3 cm |
| Min | 385 g | 121 mm | 23 mm | 27 mm | 38.7 cm |

TABLE 5A-continued

| | | 'Latitude' | | | |
|---|---|---|---|---|---|
| | Head Wt. | Head Diameter | Core Length | Core Diameter | Frame Diameter |
| Average | 507.5 g | 129.6 mm | 26.05 mm | 30.7 mm | 45.75 cm |
| Std. Dev. | 80.94 | 5.55 | 2.31 | 1.53 | 2.72 |

TABLE 5B

| | | 'PS 1501' | | | |
|---|---|---|---|---|---|
| | Head Wt. | Head Diameter | Core Length | Core Diameter | Frame Diameter |
| Max | 650 g | 151 mm | 31 mm | 33 mm | 47.5 cm |
| Min | 415 g | 124 mm | 20 mm | 27 mm | 41.1 cm |
| Average | 536 g | 135.75 mm | 23.65 mm | 29.75 mm | 44.93 cm |
| Std. Dev. | 66.64 | 7.97 | 2.72 | 2.02 | 2.44 |

TABLE 5C

| | | 'Tiber' | | | |
|---|---|---|---|---|---|
| | Head Wt. | Head Diameter | Core Length | Core Diameter | Frame Diameter |
| Max | 620 g | 159 mm | 32 mm | 34 mm | 53.4 cm |
| Min | 335 g | 112 mm | 21 mm | 27 mm | 42.4 cm |
| Average | 509 g | 130.15 mm | 24.85 mm | 30.8 mm | 48.16 cm |
| Std. Dev. | 89.35 | 11.93 | 2.94 | 1.85 | 3.02 |

Tables 6A-6C below show results of a fourth trial that compares the head weight, head diameter, core length, core diameter, and frame diameter of 20 plants of the lettuce variety 'Latitude' (Table 6A) with those of 20 plants of lettuce variety 'PS 1501' (Table 6B; unpatented; released as PI 673092) and 20 plants of lettuce variety 'Tiber' (Table 6C; unpatented; released as PI 635075). The head weights shown are total head weights.

TABLE 6A

| | | 'Latitude' | | | |
|---|---|---|---|---|---|
| | Head Wt. | Head Diameter | Core Length | Core Diameter | Frame Diameter |
| Max | 955 g | 167 mm | 68 mm | 36 mm | 55.1 cm |
| Min | 610 g | 135 mm | 41 mm | 27 mm | 45.7 cm |
| Average | 788 g | 155.55 mm | 53.6 mm | 30.65 mm | 50.835 cm |
| Std. Dev. | 90.20 | 8.30 | 7.56 | 2.66 | 2.46 |

TABLE 6B

| 'PS 1501' | Head Wt. | Head Diameter | Core Length | Core Diameter | Frame Diameter |
|---|---|---|---|---|---|
| Max | 960 g | 174 mm | 65 mm | 34 mm | 55.6 cm |
| Min | 530 g | 138 mm | 35 mm | 27 mm | 48.3 cm |
| Average | 693.75 g | 154.45 mm | 48.7 mm | 30.55 mm | 51.05 cm |
| Std. Dev. | 123.46 | 9.03 | 7.70 | 2.04 | 2.04 |

TABLE 6C

| 'Tiber' | Head Wt. | Head Diameter | Core Length | Core Diameter | Frame Diameter |
|---|---|---|---|---|---|
| Max | 885 g | 160 mm | 66 mm | 35 mm | 53.2 cm |
| Min | 480 g | 130 mm | 39 mm | 26 mm | 47.8 cm |
| Average | 647 g | 148.3 mm | 53.05 mm | 29.95 mm | 50.52 cm |
| Std. Dev. | 118.94 | 8.58 | 6.95 | 2.70 | 1.63 |

Figure 2A:
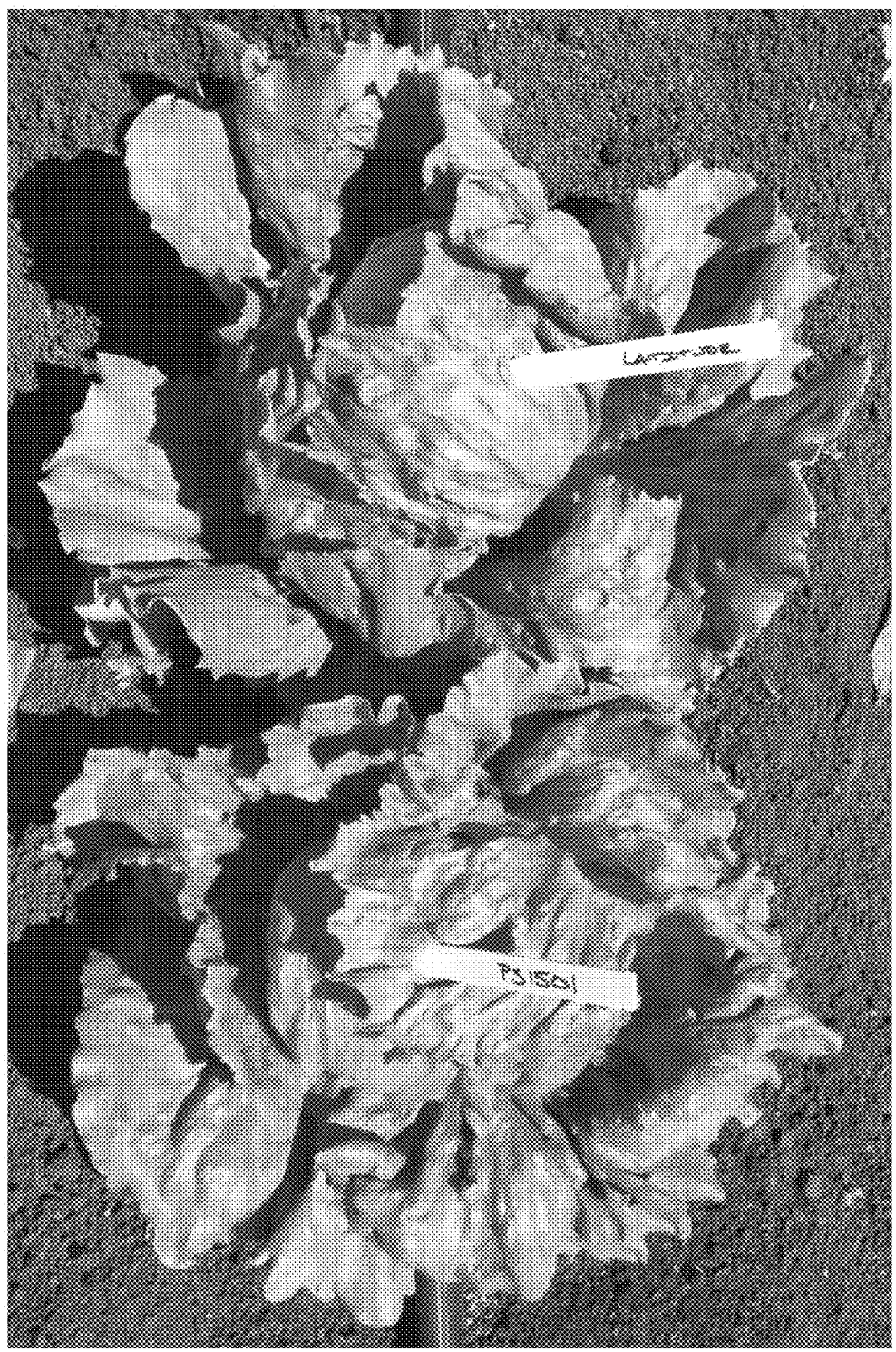
FIGS. 2A-2Q show comparisons of lettuce variety 'Latitude' with lettuce varieties 'PS 1501' (unpatented; released as PI 673092) and 'Tiber' (unpatented; released as PI 635075).
Figure 2B:
FIG. 2B shows a top view of a plant of lettuce variety 'Latitude' (top) and a plant of lettuce variety 'Tiber' (bottom).
Figure 2C:
FIG. 2C shows a bottom view of a head of lettuce variety 'Latitude' (top) and lettuce variety 'PS 1501' (bottom).
Figure 2D:
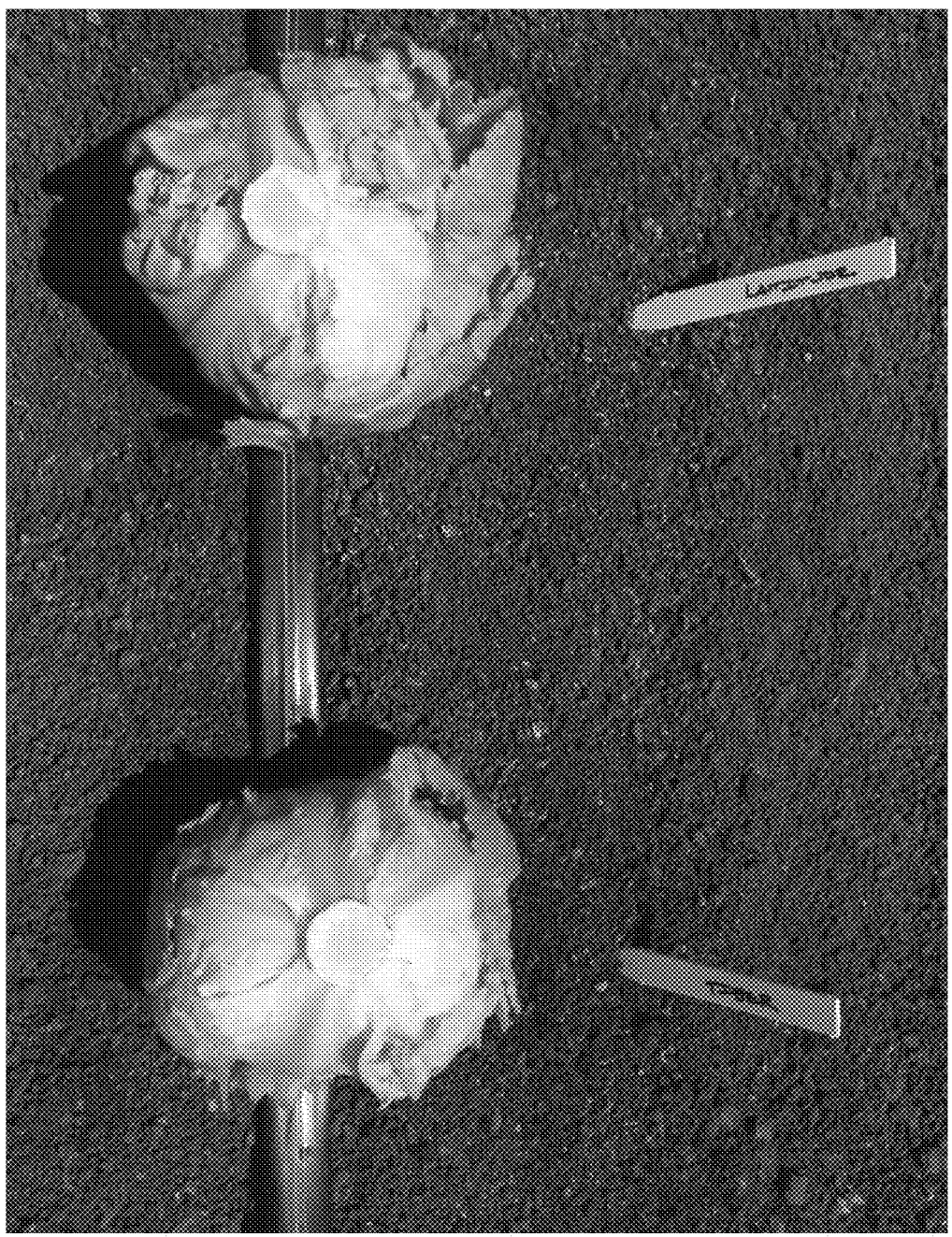
FIG. 2D shows a bottom view of a head of lettuce variety 'Latitude' (top) and lettuce variety 'Tiber' (bottom).
Figure 2E:
FIG. 2E shows a side view of a head of lettuce variety 'Latitude' (top) and a head of lettuce variety 'PS 1501' (bottom).
Figure 2F:
FIG. 2F shows a side view of a head of lettuce variety 'Latitude' (top) and a head of lettuce variety 'Tiber' (bottom).
Figure 2G:
FIG. 2G shows a cross-sectional view of a head of lettuce variety 'Latitude' (top) and a head of lettuce variety 'PS 1501' (bottom).
Figure 2H:
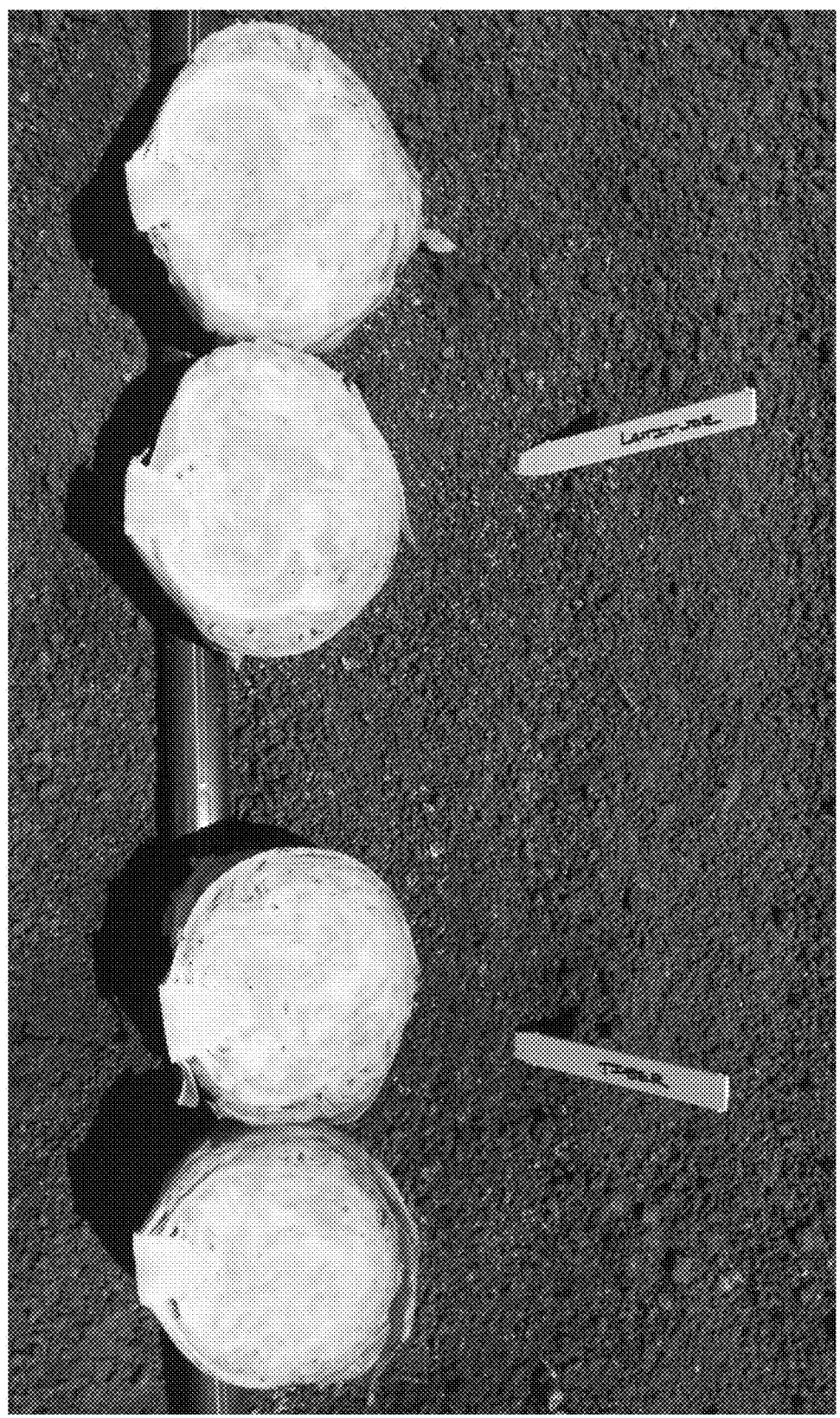
FIG. 2H shows a cross-sectional view of a head of lettuce variety 'Latitude' (top) and a head of lettuce variety 'Tiber' (bottom).
Figure 2I:
FIG. 2I shows a mature leaf of lettuce variety 'Latitude' (top) and a mature leaf of lettuce variety 'PS 1501' (bottom).
Figure 2J:
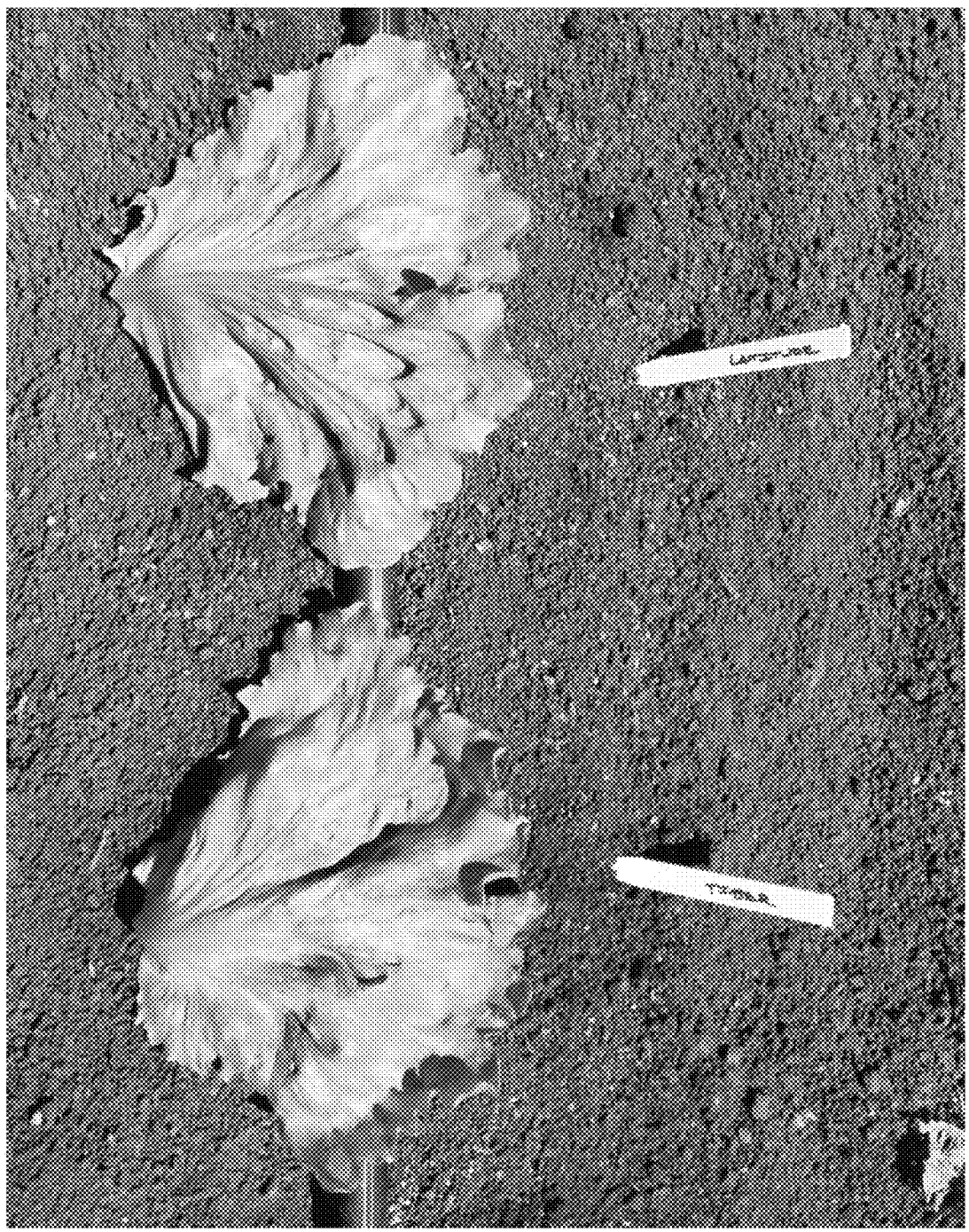
FIG. 2J shows a mature leaf of lettuce variety 'Latitude' (top) and a mature leaf of lettuce variety 'Tiber' (bottom).
Figure 2K:
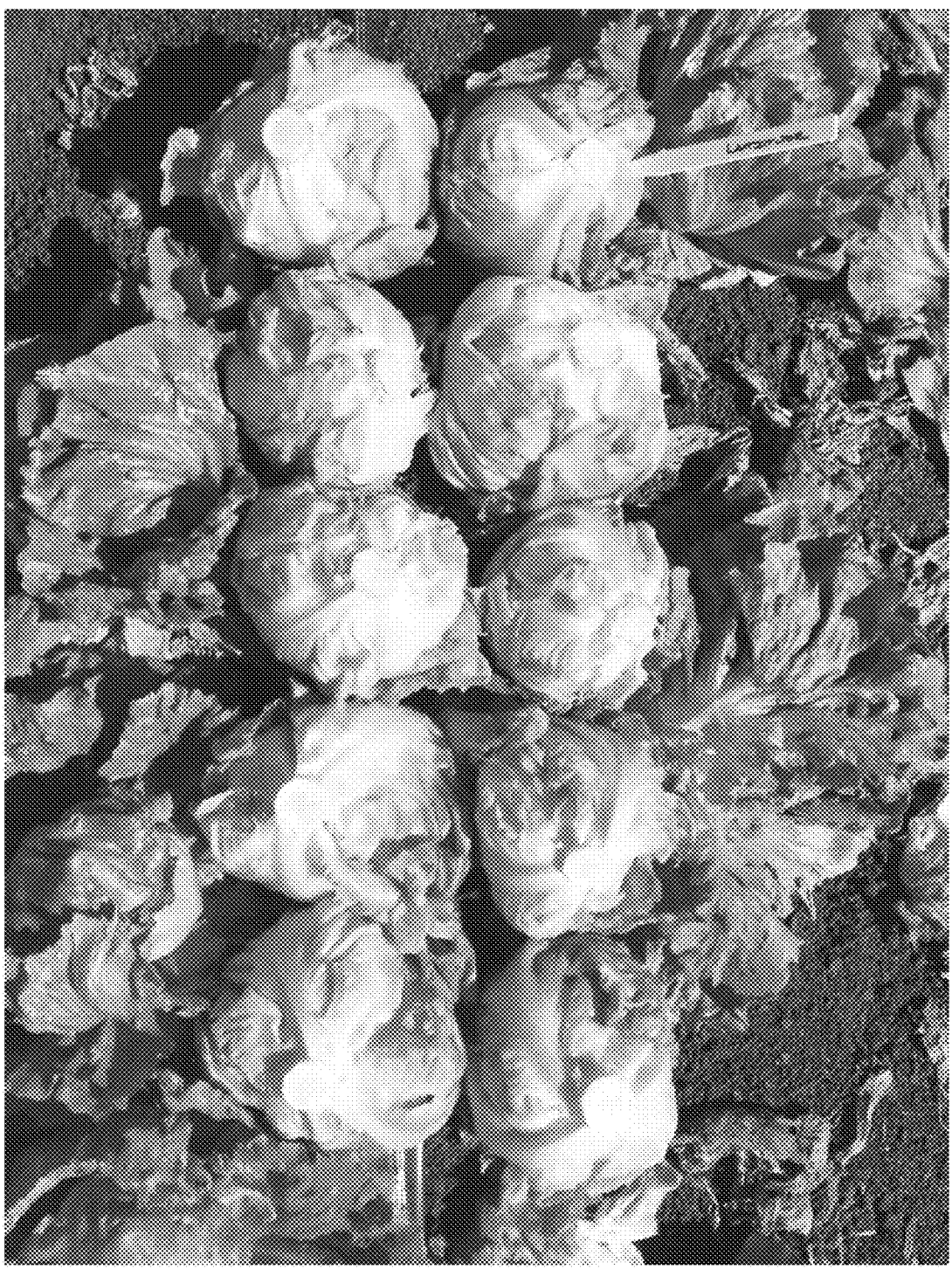
FIG. 2K shows a bottom view of heads of lettuce variety 'Latitude'.
Figure 2L:
FIG. 2L shows a bottom view of heads of lettuce variety 'PS 1501'.
Figure 2M:
FIG. 2M shows a bottom view of heads of lettuce variety 'Tiber'.
Figure 2N:
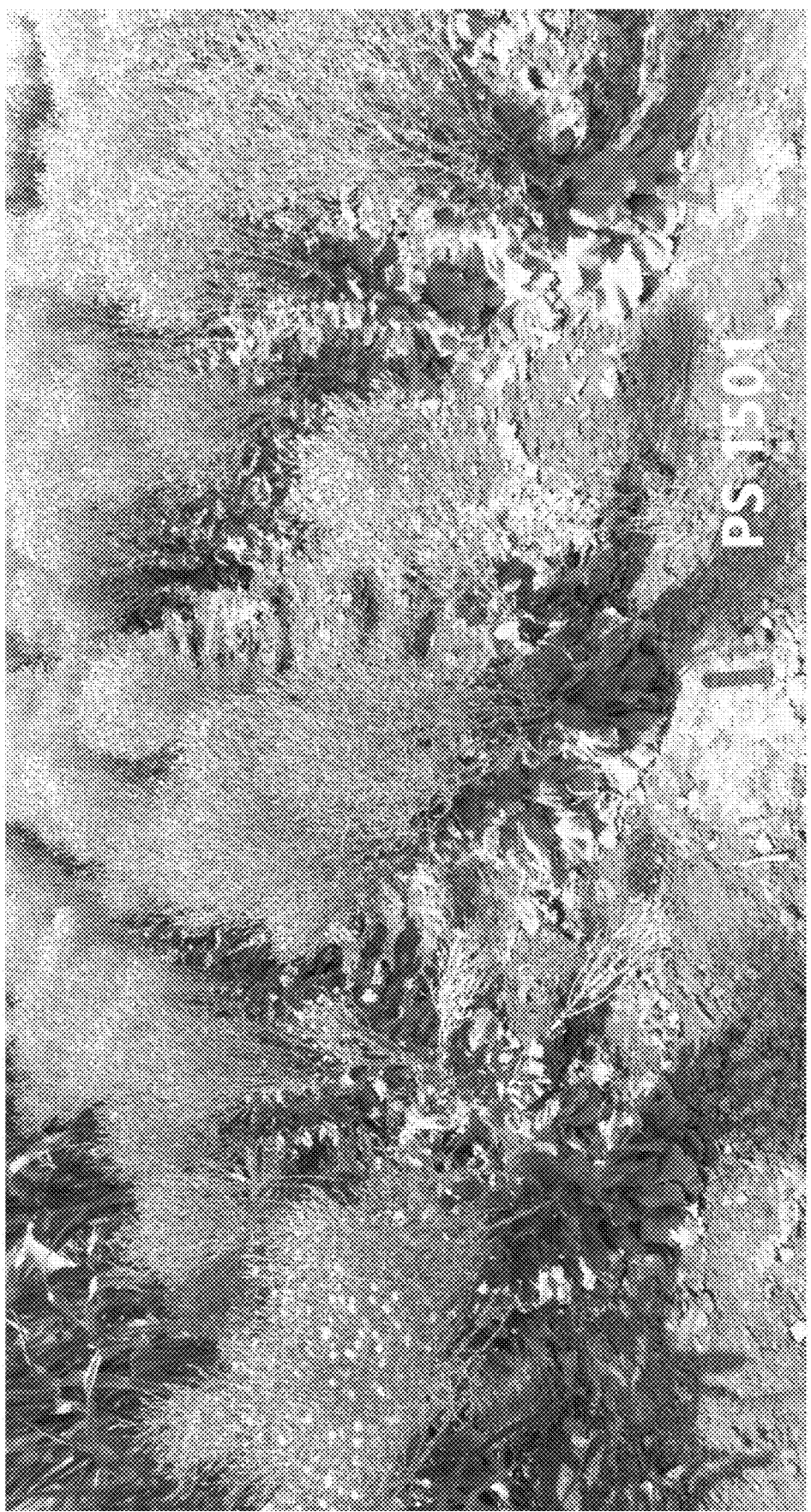
FIG. 2N shows bolting plants of lettuce variety 'PS 1501'.
Figure 20:
Figure 2P:
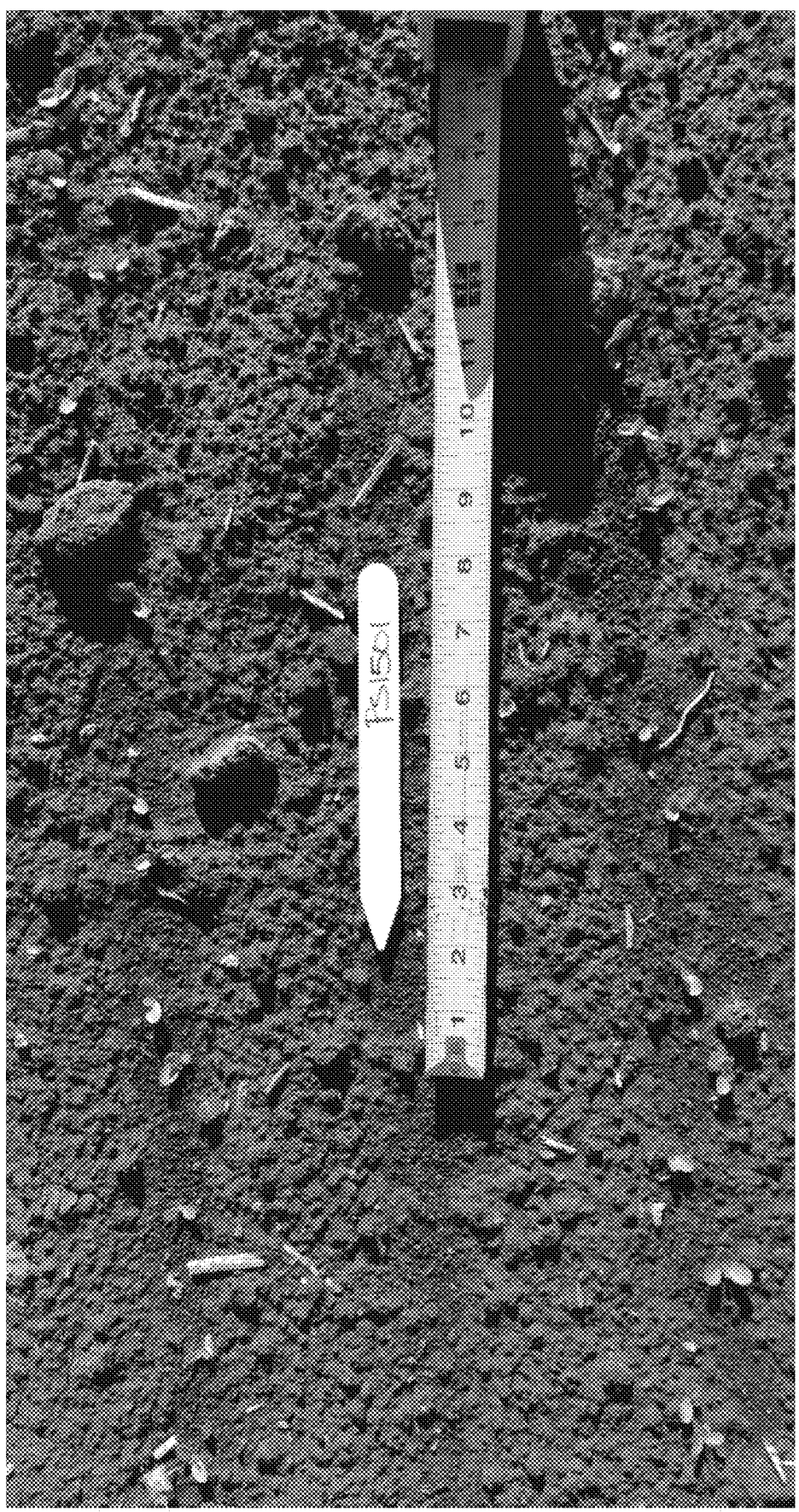
FIG. 2P shows seedlings of lettuce variety 'PS 1501'.
Figure 2Q:
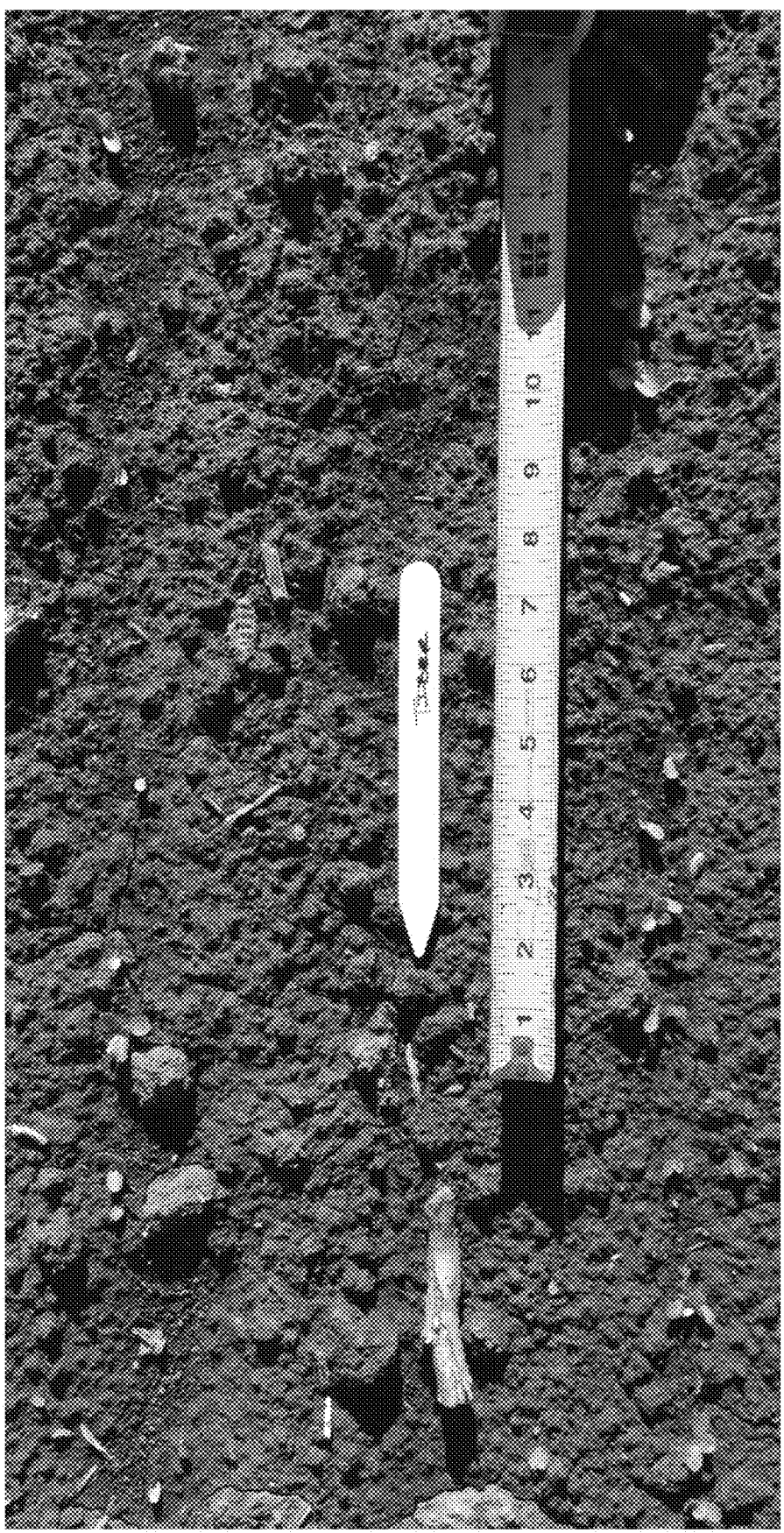
Figure 3A:
FIGS. 3A-3F show lettuce variety 'Pacific Heart'.
Figure 3B:
Figure 3C:
Figure 3D:
Figure 3E:
Figure 3F:
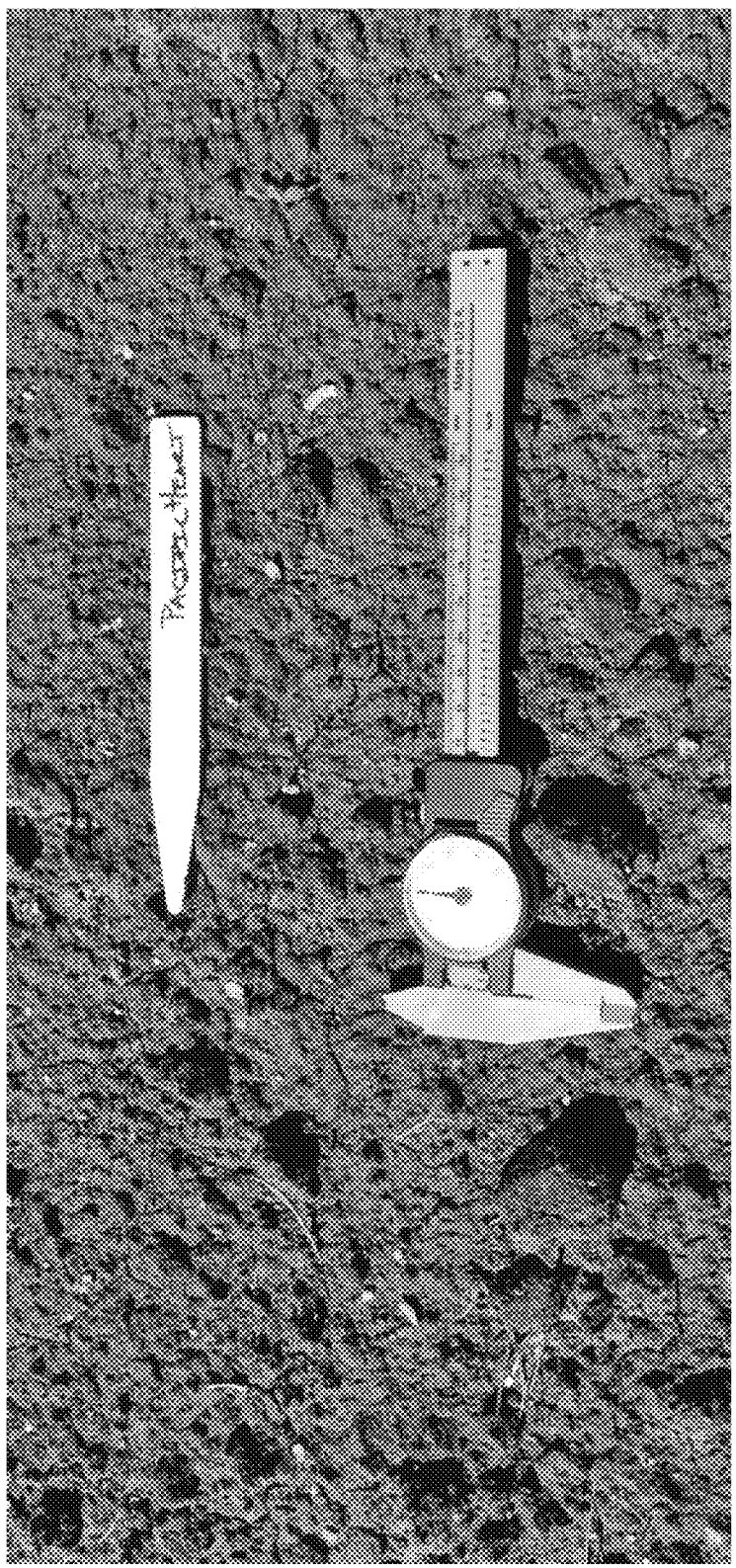

Further distinguishing features are apparent from the comparison of the variety 'Latitude' with the varieties 'PS 1501' and 'Tiber' depicted in FIGS. 2A-2Q.

Objective Description of the Variety 'Pacific Heart'

'Pacific Heart' is a romaine lettuce variety. This variety is distinct and unique to all other romaine lettuce varieties due to its resistance to *Nasonovia ribisnigri* Nr: 0 and *Fusarium* Wilt race 1, as well as characteristics including its green color, time to maturity, leaf cupping, leaf smoothness, and rib smoothness. 'Pacific Heart' has a growing season that includes spring and summer in West Coast regions of the United States as well as winter in regions in the Southwest of the United States, such the Arizona desert, and is suitable for growing in the open. FIGS. 3A-3F depict plants, hearts, and seedlings of lettuce variety 'Pacific Heart'. Lettuce variety 'Pacific Heart' is the result of numerous generations of plant selections chosen for its high degree of resistance to *Nasonovia ribisnigri* Nr: 0 and *Fusarium* Wilt race 1.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Pacific Heart'.

Lettuce variety 'Pacific Heart' has the following morphologic and other characteristics:
Plant type: Cos (i.e., romaine)
Seed:
    Color: Munsell 2.5Y 7/2 (White)
    Light dormancy: Light required
    Heat dormancy: Not susceptible
Cotyledon to Fourth Leaf Stage:
    Shape of cotyledons: Intermediate
    Shape of fourth leaf: Oval
    Fourth leaf length: 18.9 mm
    Fourth leaf width: 10.1 mm
    Fourth leaf index (length/width×10): 18.8
    Apical margin: Entire
    Basal margin: Moderately dentate
    Green color: Light green
    Anthocyanin distribution: Absent
    Cupping: Uncupped
    Reflexing: Apical margins
Mature Leaves:
    Margin:
        Incision depth (deepest penetration of the margin): Absent/shallow
        Indentation (finest divisions of the margin): Entire
        Undulation of apical margin: Absent/slight
    Green color: Munsell 5GY 5/8 (Light green)
    Anthocyanin distribution: Absent
    Glossiness: Dull
    Blistering: Moderate
    Thickness: Intermediate
    Trichomes: Absent (smooth)

Plant:
  Weight: 672.7 g
  Spread of frame leaves: 39 cm
  Heart diameter (market trimmed): 32.6 cm
  Heart shape: Elongate
  Heart size class: Large
  Heart firmness: Moderate
Butt:
  Shape: Rounded
  Midrib: Prominently raised
Core:
  Diameter at base of head: 34.6 mm
  Ratio of heart diameter/core diameter: 9.4
  Height from base of heart to apex: 78.5 mm
Bolting:
  Number of days from first water to seed stalk emergence under summer conditions: 69
  Bolting class: Rapid
  Mature seed stalk height: 83.7 cm
  Mature seed stalk spread: 31.5 cm
  Bolter leaves: Curved
  Margin: Dentate
  Bolter habit:
    Terminal inflorescence: Absent
    Lateral shoots: Present
    Basal side shoots: Present
Disease Resistance:
  Lettuce Big-Vein Virus (LBVV): Susceptible
  Lettuce Mosaic Virus (LMV) strain Ls-1: Susceptible
  Powdery Mildew: Susceptible
  Corky Root Rot: Susceptible
  Downy Mildew (*Bremia lactucae*) (B1): Resistant to isolates B1: 16, B1: 20, B1: 21, B1: 26, B1: 27, B1: 29, B1: 30, and B1: 33
  *Fusarium* Wilt (*Fusarium oxysporum* f. sp. *lactucae*) race 1: Resistant
Pest Resistance:
  *Nasonovia ribisnigri* biotype 0 (Nr: 0): Resistant
Stress Resistance:
  Tipburn: Moderately resistant
  Heat: Susceptible
  Cold: Susceptible
  Pink rib: Susceptible
  Rusty brown discoloration: Susceptible
  Internal rib necrosis: Susceptible
Comparisons to Other Lettuce Variety Table 7 below compares characteristics of lettuce variety 'Pacific Heart' with the lettuce variety 'Salvius' (U.S. Pat. No. 8,389,810, variety designation "41-49 RZ"). Column 1 lists the characteristics, column 2 shows the characteristics for lettuce variety 'Pacific Heart', and column 3 shows the characteristics for lettuce variety 'Salvius'.

TABLE 7

| Characteristic | 'Pacific Heart' | 'Salvius' |
|---|---|---|
| Plant weight | 672.7 g | 705.6 g |
| Green color of mature leaves | Munsell 5GY 5/8 | Munsell 5GY 4/6 |
| Heart diameter | 32.6 cm | 33.7 cm |
| Core diameter | 34.6 mm | 35 mm |
| Core height at base of heart to apex | 78.5 mm | 58.7 mm |
| Mature seed stalk height | 83.7 cm | 91.6 cm |
| Mature seed stalk spread | 31.5 cm | 32.9 cm |

Table 8 below compares characteristics of lettuce variety 'Pacific Heart' with the lettuce variety 'Vicious' (U.S. Pat. No. 9,913,452, variety designation "NUN 06117 LTL"). Column 1 lists the characteristics, column 2 shows the characteristics for lettuce variety 'Pacific Heart', and column 3 shows the characteristics for lettuce variety 'Vicious'.

TABLE 8

| Characteristic | 'Pacific Heart' | 'Vicious' |
|---|---|---|
| Plant weight | 672.7 g | 650 g |
| Green color of mature leaves | Munsell 5GY 5/8 | Munsell 5GY 4/4 |
| Spread of frame leaves | 39 cm | 39.1 cm |
| Heart diameter | 32.6 cm | 33.1 cm |
| Core diameter | 34.6 mm | 35.8 mm |
| Core height at base of heart to apex | 78.5 mm | 53.4 mm |
| Mature seed stalk height | 83.7 cm | 102.8 cm |
| Mature seed stalk spread | 31.5 cm | 45.2 cm |

Tables 9A-9C below show results of a first trial that compares the head weight, heart length, core length, core diameter, and frame diameter of 20 plants of the lettuce variety 'Pacific Heart' (Table 9A) with those of 20 plants of lettuce variety 'Salvius' (Table 9B; U.S. Pat. No. 8,389,810, variety designation "41-49 RZ") and 20 plants of lettuce variety 'Vicious' (Table 9C; U.S. Pat. No. 9,913,452, variety designation "NUN 06117 LTL"). The weights shown are of the whole plant (i.e., heart with the outer leaves attached), which is referred to as a head when sold (e.g., as a boxed product).

TABLE 9A

| 'Pacific Heart' | Heart Wt. | Heart Length | Core Length | Core Diameter | Frame Diameter |
|---|---|---|---|---|---|
| Max | 880 g | 415 mm | 120 mm | 40 mm | 43.1 cm |
| Min | 595 g | 370 mm | 60 mm | 34 mm | 35.5 cm |
| Average | 714.25 g | 396.25 mm | 94.7 mm | 37.95 mm | 38.505 cm |
| Std. Dev | 85.78 | 12.66 | 15.25 | 1.93 | 2.12 |

TABLE 9B

| 'Salvius' | Heart Wt. | Heart Length | Core Length | Core Diameter | Frame Diameter |
|---|---|---|---|---|---|
| Max | 840 g | 430 mm | 140 mm | 40 mm | 42.4 cm |
| Min | 540 g | 370 mm | 50 mm | 32 mm | 34.3 cm |
| Average | 744.25 g | 397.5 mm | 84.7 mm | 36.25 mm | 38.5 cm |
| Std. Dev | 77.52 | 18.10 | 24.08 | 2.31 | 2.40 |

TABLE 9C

| 'Vicious' | Heart Wt. | Heart Length | Core Length | Core Diameter | Frame Diameter |
|---|---|---|---|---|---|
| Max | 850 g | 475 mm | 64 mm | 41 mm | 40.4 cm |
| Min | 590 g | 370 mm | 46 mm | 30 mm | 32.9 cm |
| Average | 694.5 g | 408.5 mm | 56.05 mm | 36.05 mm | 35.695 cm |
| Std. Dev | 79.72 | 23.79 | 5.10 | 3.30 | 2.58 |

Tables 10A-10C below show results of a second trial that compares the head weight, heart length, core length, core diameter, and frame diameter of 20 plants of the lettuce variety 'Pacific Heart' (Table 10A) with those of 20 plants of lettuce variety 'Salvius' (Table 10B; U.S. Pat. No. 8,389,810, variety designation "41-49 RZ") and 20 plants of lettuce variety 'Vicious' (Table 10C; U.S. Pat. No. 9,913,452, variety designation "NUN 06117 LTL"). The weights shown are of the whole plant (i.e., heart with the outer leaves attached), which is referred to as a head when sold (e.g., as a boxed product).

TABLE 10A

| 'Pacific Heart' | Heart Wt. | Heart Length | Core Length | Core Diameter | Frame Diameter |
|---|---|---|---|---|---|
| Max | 1000 g | 360 mm | 115 mm | 41 mm | 38.5 cm |
| Min | 530 g | 290 mm | 50 mm | 32 mm | 33.5 cm |
| Average | 717.8 g | 331.3 mm | 75.6 mm | 37.25 mm | 35.73 cm |
| Std. Dev | 97.82 | 20.71 | 17.74 | 3.13 | 1.66 |

TABLE 10B

| 'Salvius' | Heart Wt. | Heart Length | Core Length | Core Diameter | Frame Diameter |
|---|---|---|---|---|---|
| Max | 1110 g | 390 mm | 103 mm | 42 mm | 40.1 cm |
| Min | 655 g | 340 mm | 46 mm | 30 mm | 32.1 cm |
| Average | 920.55 g | 361.25 mm | 75.8 mm | 38.85 mm | 34.645 cm |
| Std. Dev | 131.10 | 14.13 | 14.46 | 2.76 | 2.06 |

TABLE 10C

| 'Vicious' | Heart Wt. | Heart Length | Core Length | Core Diameter | Frame Diameter |
|---|---|---|---|---|---|
| Max | 805 g | 390 mm | 50 mm | 40 mm | 43.4 cm |
| Min | 490 g | 320 mm | 28 mm | 29 mm | 34.8 cm |
| Average | 650.25 g | 355 mm | 39.5 mm | 35.95 mm | 39.185 cm |
| Std. Dev | 93.76 | 16.62 | 7.58 | 3.10 | 2.09 |

Tables 11A-11C below show results of a third trial that compares the head weight, heart length, core length, core diameter, and frame diameter of 20 plants of the lettuce variety 'Pacific Heart' (Table 11A) with those of 20 plants of lettuce variety 'Salvius' (Table 11B; U.S. Pat. No. 8,389,810, variety designation "41-49 RZ") and 20 plants of lettuce variety 'Vicious' (Table 11C; U.S. Pat. No. 9,913,452, variety designation "NUN 06117 LTL"). The weights shown are of the whole plant (i.e., heart with the outer leaves attached), which is referred to as a head when sold (e.g., as a boxed product).

TABLE 11A

| 'Pacific Heart' | Heart Wt. | Heart Length | Core Length | Core Diameter | Frame Diameter |
|---|---|---|---|---|---|
| Max | 916 g | 256 mm | 82 mm | 36 mm | 50.2 cm |
| Min | 350 g | 215 mm | 48 mm | 25 mm | 37.1 cm |
| Average | 690.55 g | 241.45 mm | 61.95 mm | 32.4 mm | 44.22 cm |
| Std. Dev | 142.09 | 11.18 | 9.76 | 3.15 | 3.58 |

TABLE 11B

| 'Salvius' | Heart Wt. | Heart Length | Core Length | Core Diameter | Frame Diameter |
|---|---|---|---|---|---|
| Max | 720 g | 270 mm | 45 mm | 40 mm | 49.7 cm |
| Min | 400 g | 195 mm | 24 mm | 23 mm | 39.4 cm |
| Average | 581 g | 243.85 mm | 35.05 mm | 32.65 mm | 44.035 cm |
| Std. Dev | 80.29 | 20.46 | 6.86 | 5.12 | 3.20 |

TABLE 11C

| 'Vicious' | Heart Wt. | Heart Length | Core Length | Core Diameter | Frame Diameter |
|---|---|---|---|---|---|
| Max | 925 g | 270 mm | 65 mm | 56 mm | 48.1 cm |
| Min | 550 g | 194 mm | 25 mm | 25 mm | 39.1 cm |
| Average | 672 g | 227.35 mm | 42.85 mm | 41.1 mm | 43.765 cm |
| Std. Dev | 97.80 | 21.94 | 13.25 | 8.94 | 2.54 |

Tables 12A-12C below show results of a fourth trial that compares the head weight, heart length, core length, core diameter, and frame diameter of 20 plants of the lettuce variety 'Pacific Heart' (Table 12A) with those of 20 plants of lettuce variety 'Salvius' (Table 12B; U.S. Pat. No. 8,389,810, variety designation "41-49 RZ") and 20 plants of lettuce variety 'Vicious' (Table 12C; U.S. Pat. No. 9,913,452, variety designation "NUN 06117 LTL"). The weights shown are of the whole plant (i.e., heart with the outer leaves attached), which is referred to as a head when sold (e.g., as a boxed product).

TABLE 12A

| 'Pacific Heart' | Heart Wt. | Heart Length | Core Length | Core Diameter | Frame Diameter |
|---|---|---|---|---|---|
| Max | 825 g | 371 mm | 101 mm | 36 mm | 40.1 cm |
| Min | 425 g | 304 mm | 64 mm | 27 mm | 34.2 cm |
| Average | 568 g | 333.9 mm | 79.95 mm | 30.9 mm | 37.505 cm |
| Std. Dev | 104.29 | 17.34 | 9.28 | 2.59 | 1.64 |

TABLE 12B

| 'Salvius' | Heart Wt. | Heart Length | Core Length | Core Diameter | Frame Diameter |
|---|---|---|---|---|---|
| Max | 675 g | 381 mm | 45 mm | 35 mm | 40.4 cm |
| Min | 445 g | 321 mm | 30 mm | 29 mm | 35.6 cm |
| Average | 576.75 g | 345.1 mm | 39.25 mm | 32.4 mm | 38.56 cm |
| Std. Dev | 53.10 | 16.23 | 4.48 | 1.64 | 1.45 |

TABLE 12C

| 'Vicious' | Heart Wt. | Heart Length | Core Length | Core Diameter | Frame Diameter |
|---|---|---|---|---|---|
| Max | 685 g | 363 mm | 97 mm | 33 mm | 40.7 cm |
| Min | 420 g | 297 mm | 58 mm | 27 mm | 34.8 cm |
| Average | 583.25 g | 332.55 mm | 75.05 mm | 29.95 mm | 37.845 cm |
| Std. Dev | 70.72 | 20.05 | 13.12 | 1.96 | 1.64 |

Figure 4A:
FIGS. 4A-4V show comparisons between lettuce varieties 'Pacific Heart', 'Vicious', and 'Salvius' (U.S. Pat. No. 8,389,810, variety designation "41-49 RZ").
Figure 4B:
FIG. 4B shows a bottom view of a head of lettuce variety 'Vicious'.
Figure 4C:
FIG. 4C shows a cross-sectional view of a head of lettuce variety 'Vicious'.
Figure 4D:
FIG. 4D shows a bottom view of heads of lettuce variety 'Vicious'.
Figure 4E:
FIG. 4E shows a top view of plants of lettuce variety 'Salvius'.
Figure 4F:
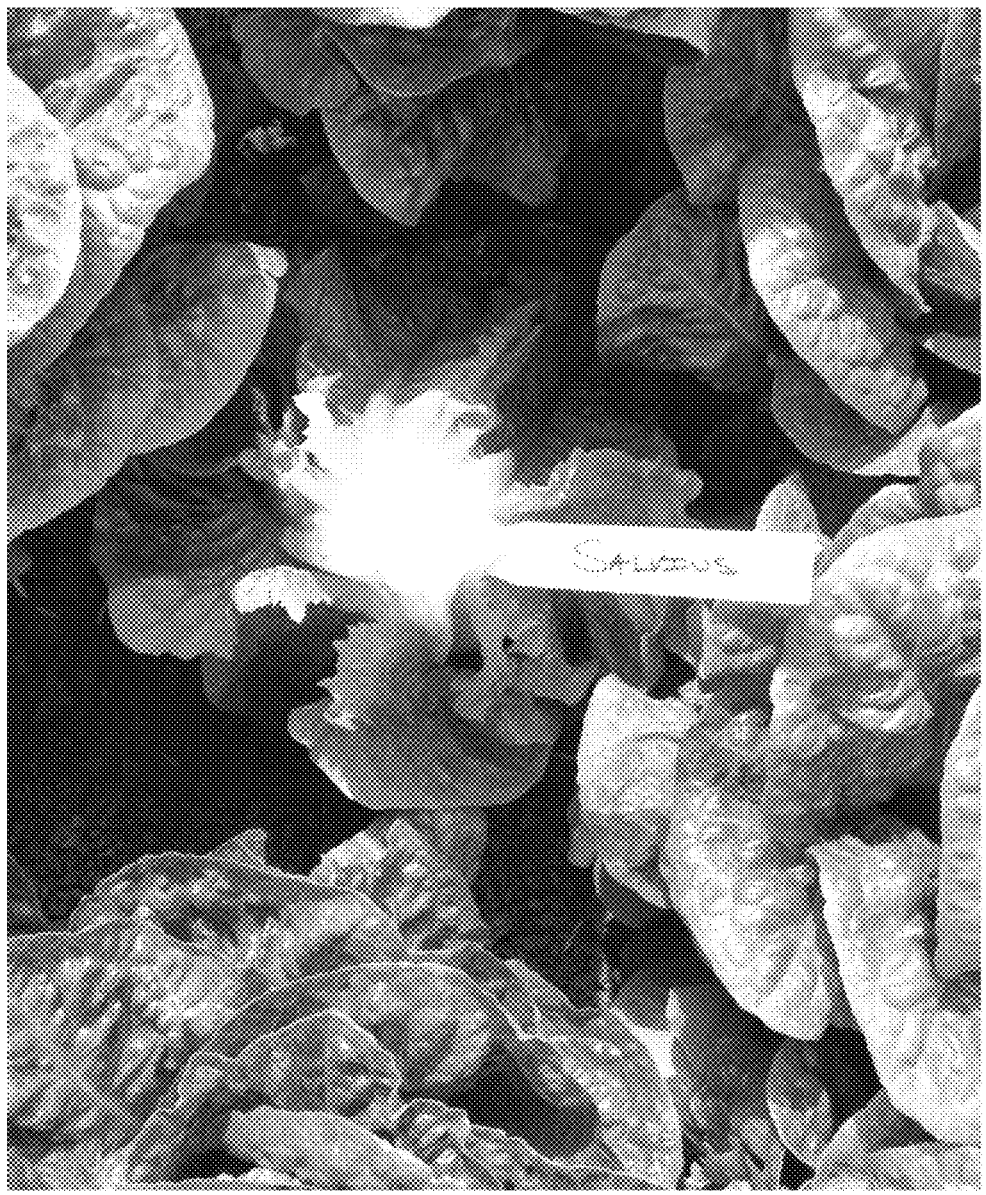
FIG. 4F shows a bottom view of a head of lettuce variety 'Salvius'.
Figure 4G:
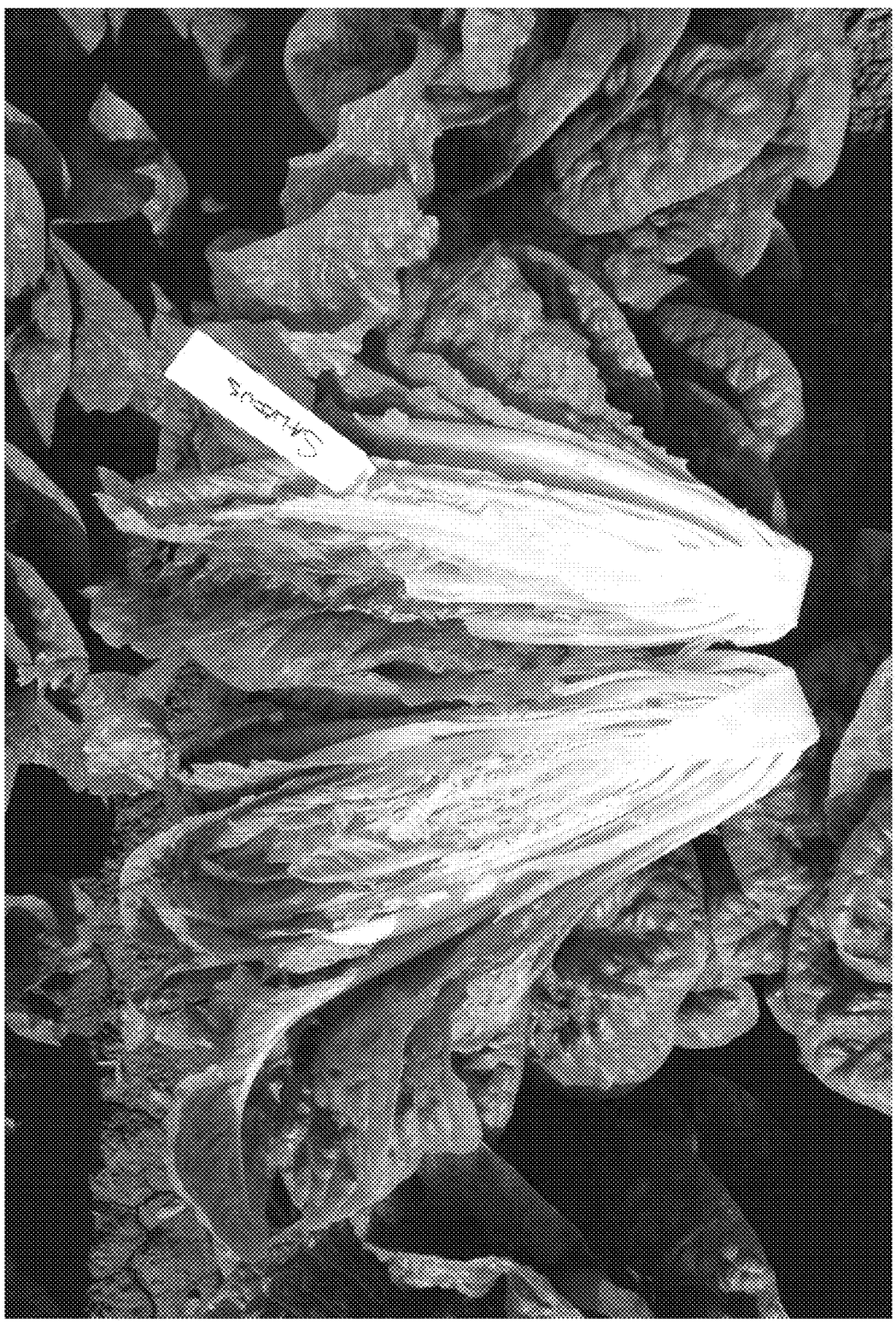
FIG. 4G shows a cross-sectional view of a head of lettuce variety 'Salvius'.
Figure 4H:
FIG. 4H shows a bottom view of heads of lettuce variety 'Salvius'.
Figure 4I:
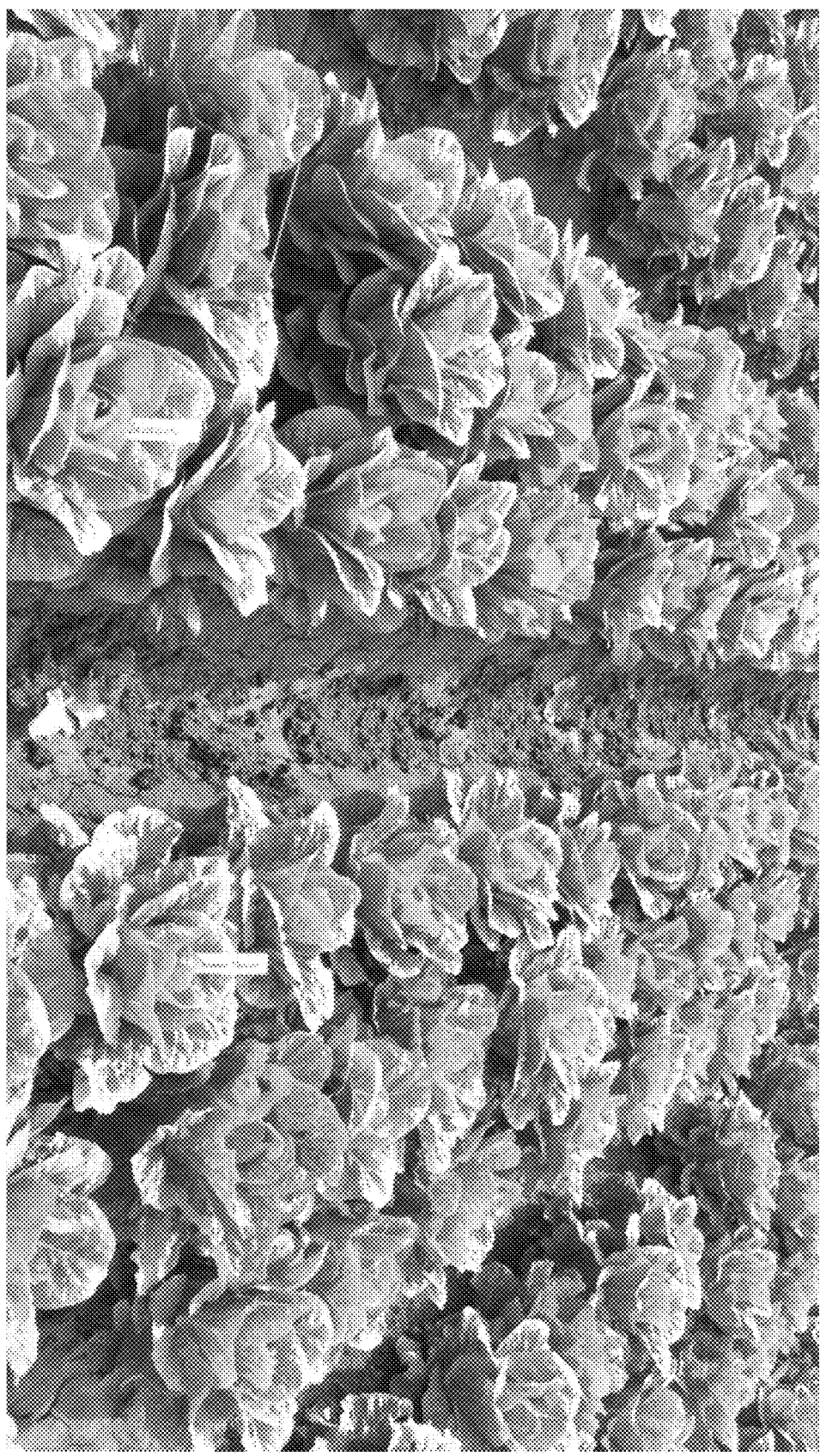
FIG. 4I shows plants of lettuce varieties 'Vicious' (top) and 'Pacific Heart' (bottom).
Figure 4J:
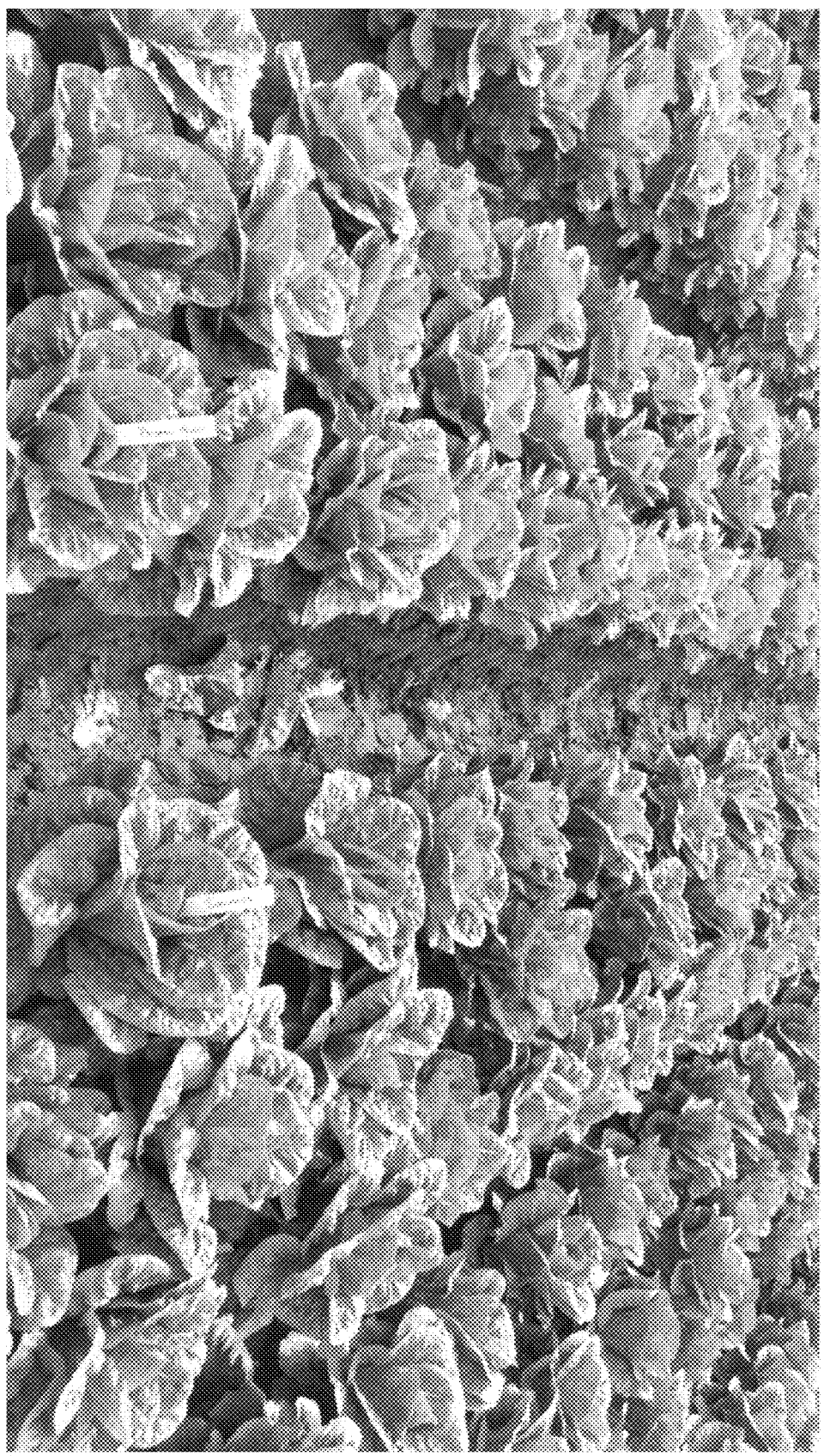
FIG. 4J shows plants of lettuce varieties 'Pacific Heart' (top) and 'Salvius' (bottom).
Figure 4K:
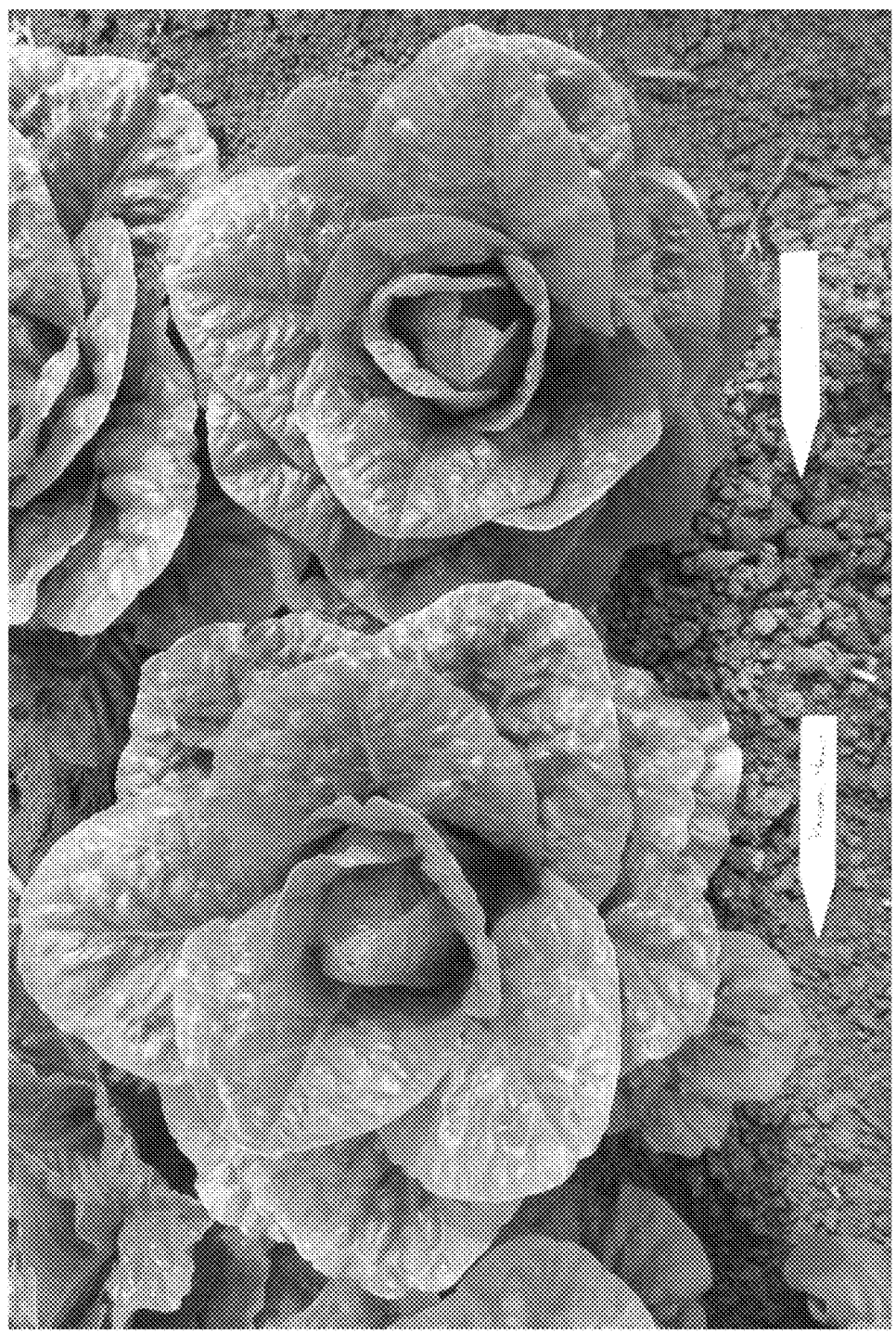
FIG. 4K shows a top view of heads of lettuce varieties 'Pacific Heart' (left) and 'Vicious' (right).
Figure 4L:
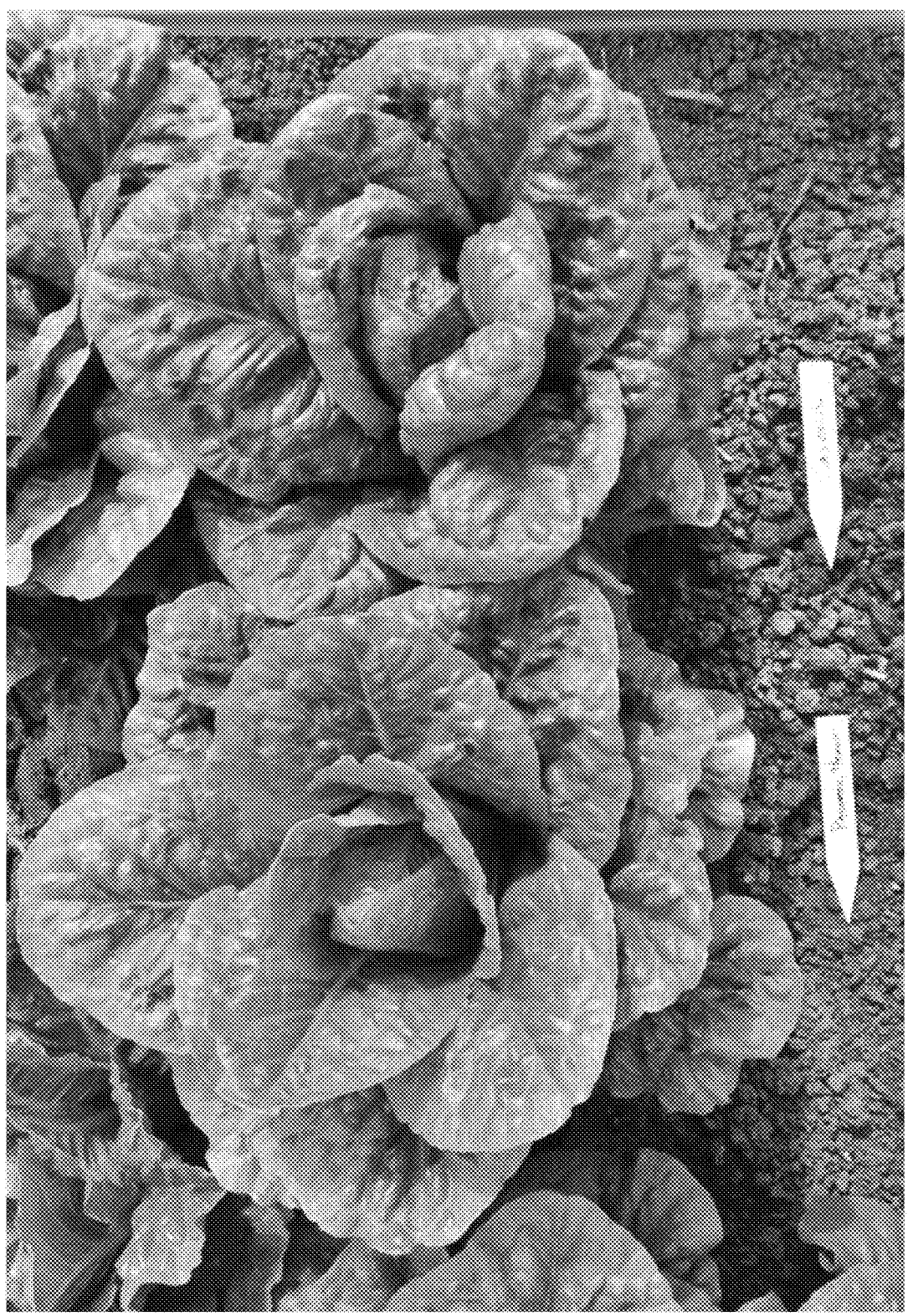
FIG. 4L shows a top view of heads of lettuce varieties 'Pacific Heart' (left) and 'Salvius' (right).
Figure 4M:
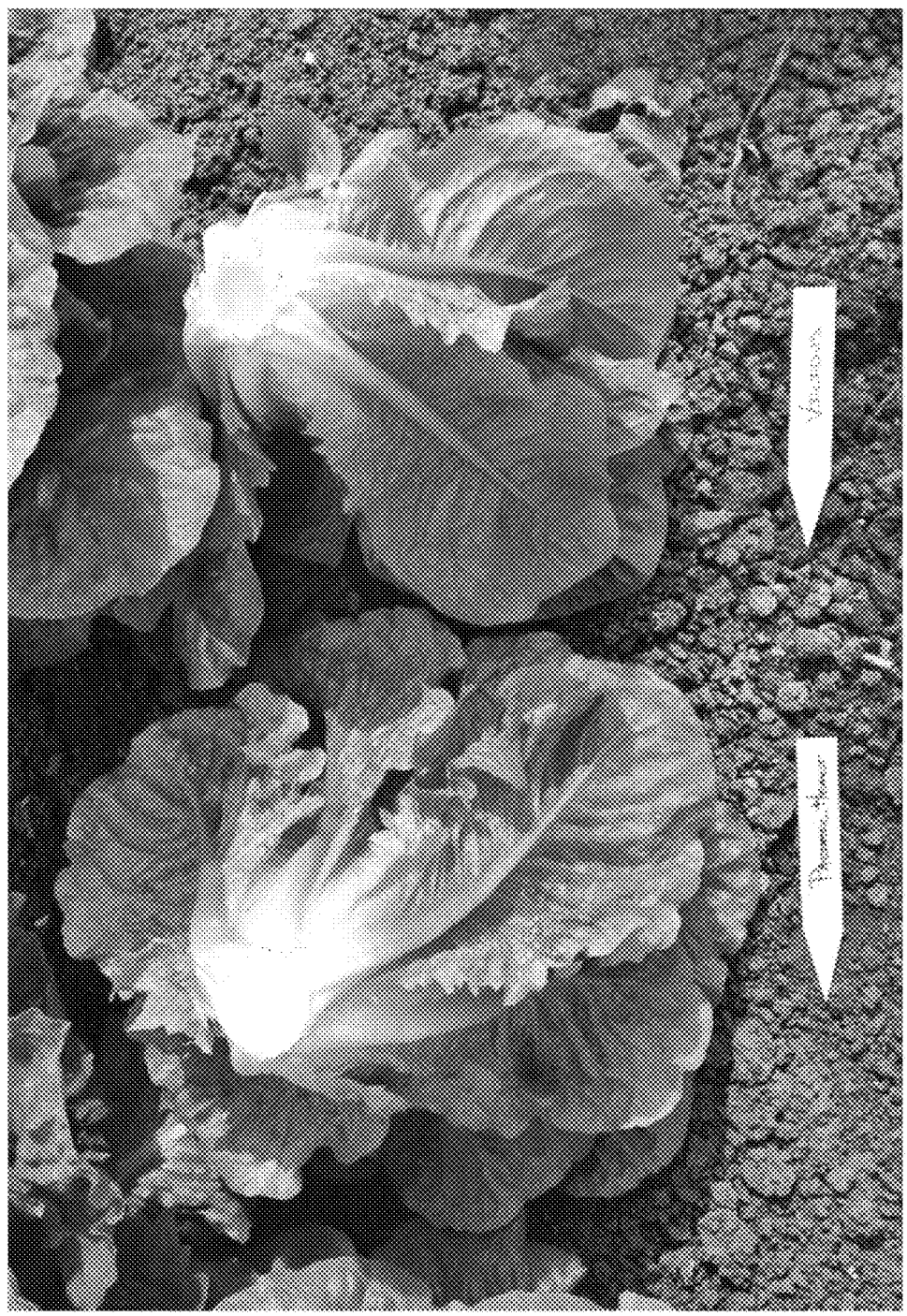
FIG. 4M shows a bottom view of heads of lettuce varieties 'Pacific Heart' (left) and 'Vicious' (right).
Figure 4N:
FIG. 4N shows a bottom view of heads of lettuce varieties 'Pacific Heart' (left) and 'Salvius' (right).
Figure 40:
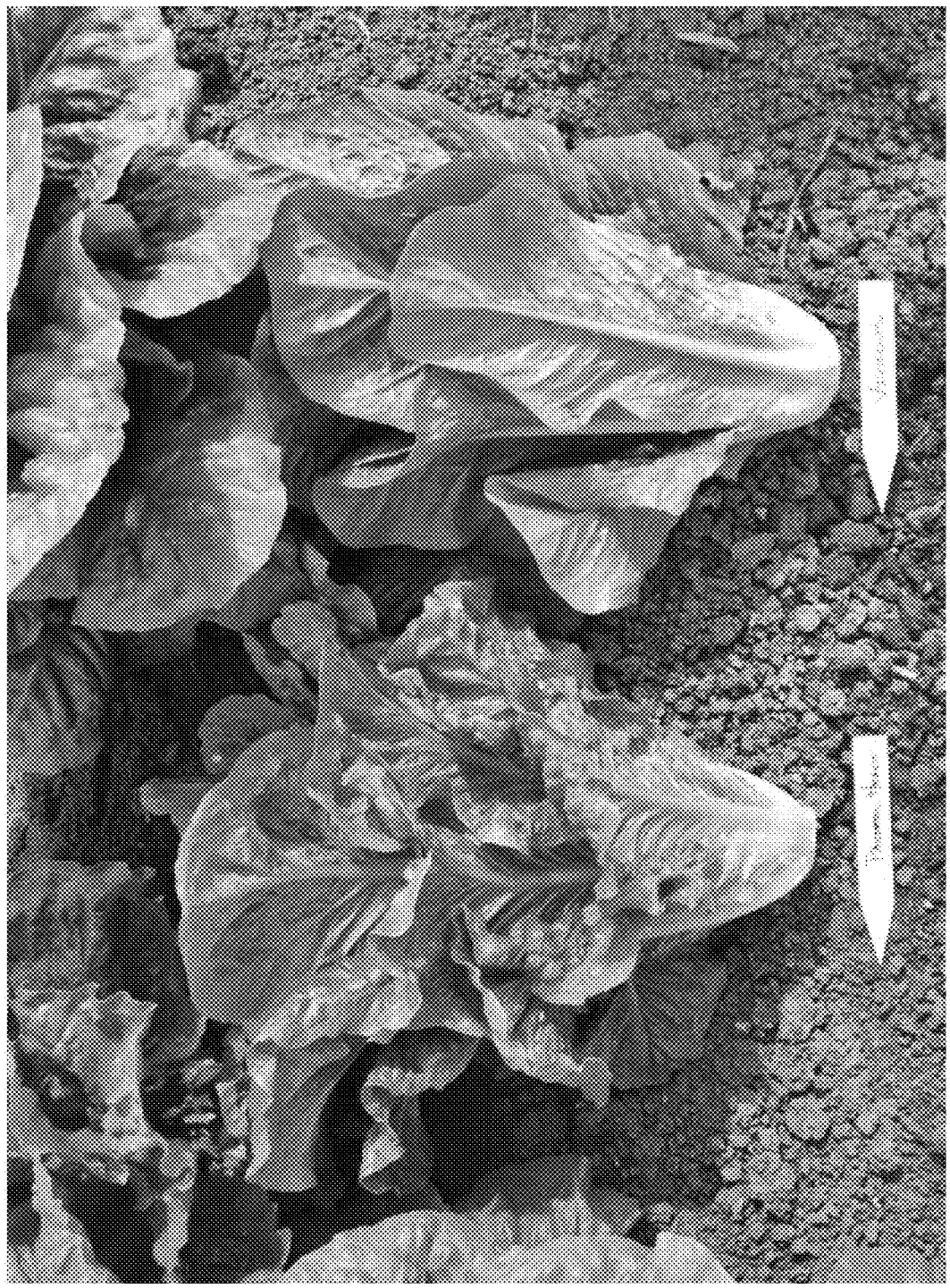
Figure 4P:
FIG. 4P shows hearts of lettuce varieties 'Pacific Heart' (left) and 'Salvius' (right).
Figure 4Q:
FIG. 4Q shows a cross-sectional view of hearts of lettuce varieties 'Pacific Heart' (left) and 'Vicious' (right).
Figure 4R:
FIG. 4R shows a cross-sectional view of hearts of lettuce varieties 'Pacific Heart' (left) and 'Salvius' (right).
Figure 4S:
FIG. 4S shows bolting plants of lettuce variety 'Vicious'.
Figure 4T:
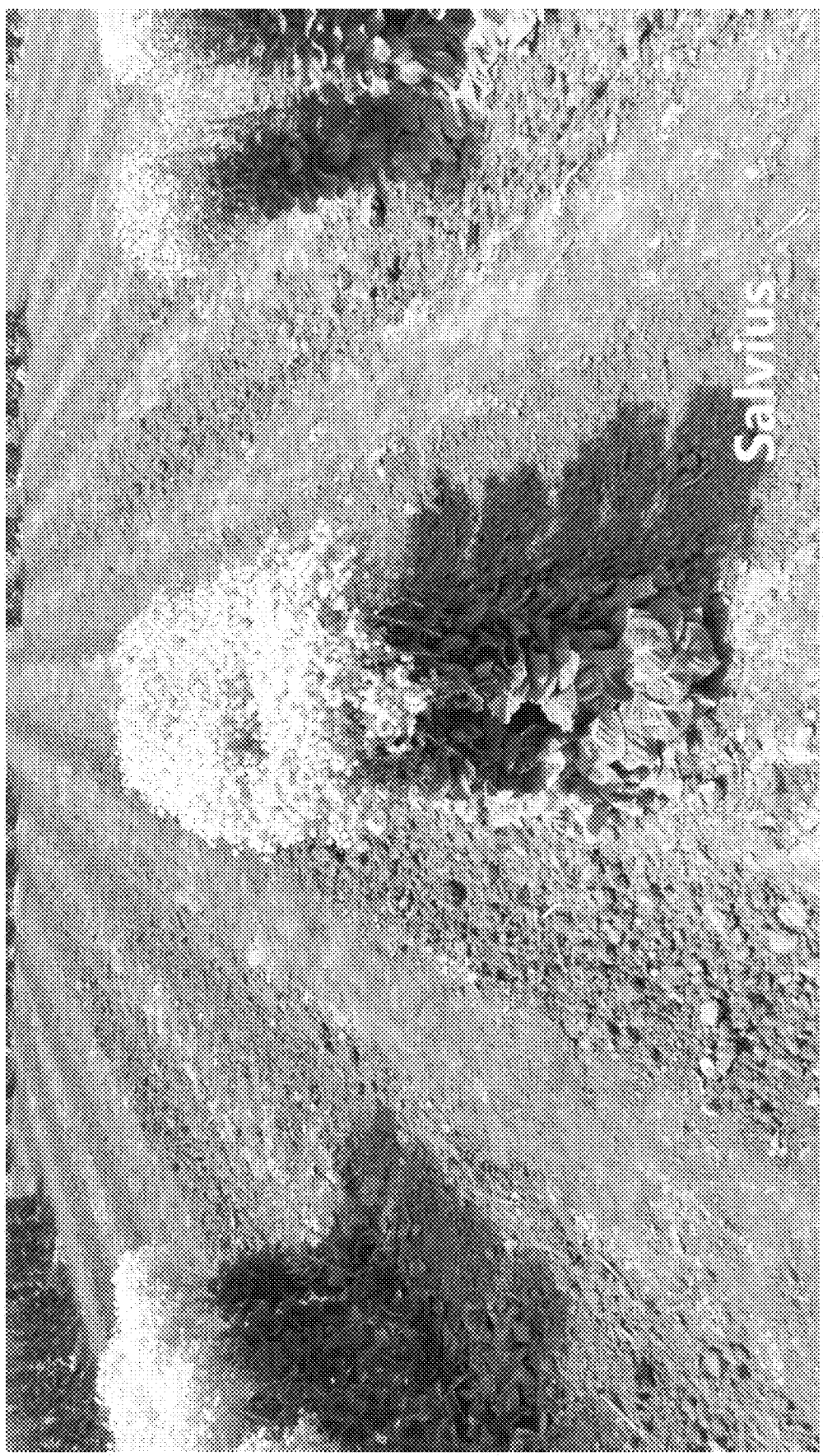
FIG. 4T shows bolting plants of lettuce variety 'Salvius'.
Figure 4U:
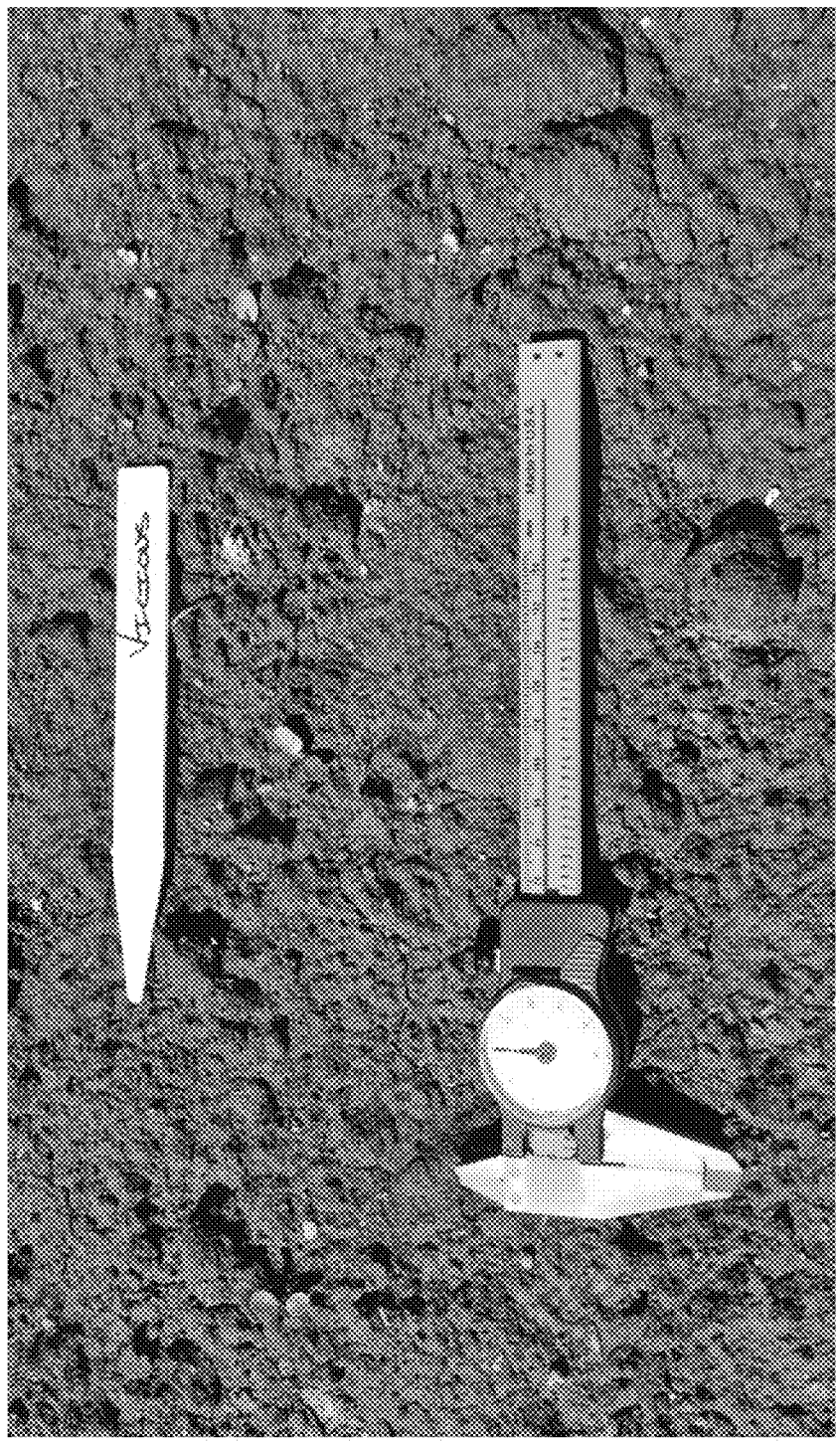
FIG. 4U shows seedlings of lettuce variety 'Vicious'.
Figure 4V:
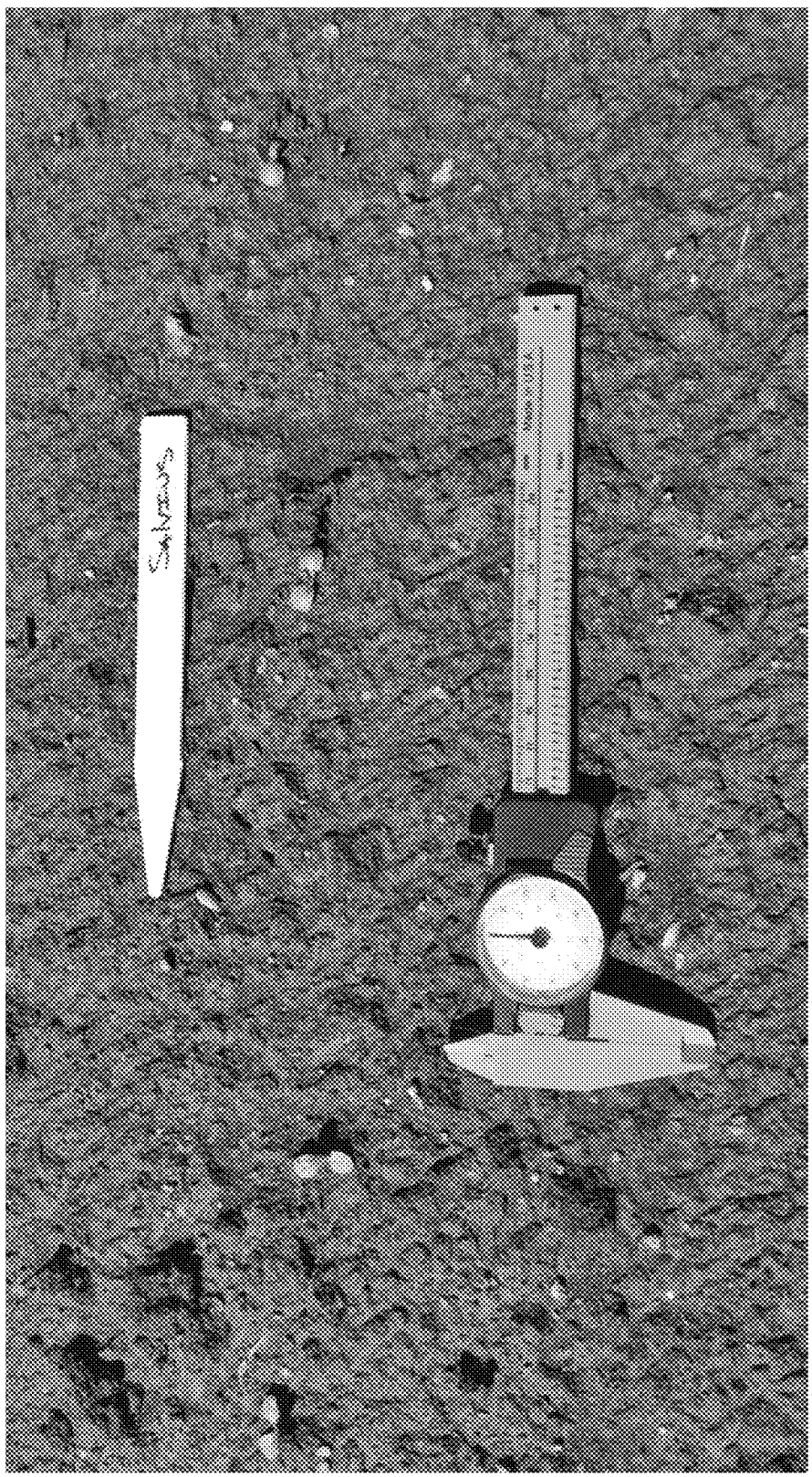

Further distinguishing features are apparent from the comparison of the varieties 'Pacific Heart', 'Salvius', and 'Vicious' depicted in FIGS. 4A-4V.

Objective Description of the Variety 'PS 1525'

'PS 1525' is an iceberg lettuce variety. This variety is distinct and unique to all other iceberg lettuce varieties due to its resistance to *Fusarium* Wilt race 1, as well as characteristics including its uniformity, weight, head diameter, and core diameter. 'PS 1525' has a growing season that includes summer and fall in West Coast regions of the United States as well as spring in regions in the Southwest of the United States, such the Arizona desert, and is suitable for growing in the open. Lettuce variety 'PS 1525' is the result of numerous generations of plant selections chosen for its resistance to *Fusarium* Wilt race 1.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'PS 1525'.

Lettuce variety 'PS 1525' has the following morphologic and other characteristics:

Plant type: Crisp (i.e., iceberg)
Seed:
   Color: Black (grey brown)
   Light dormancy: Light not required
   Heat dormancy: Susceptible
Cotyledon to Fourth Leaf Stage:
   Shape of cotyledons: Spatulate
   Shape of fourth leaf: Elongated
   Fourth leaf length: 18.8 mm
   Fourth leaf width: 9.5 mm
   Fourth leaf index (length/width×10): 19.9
   Apical margin: Finely dentate
   Basal margin: Moderately dentate
   Green color: Medium green
   Anthocyanin distribution: Absent
   Cupping: Slight
   Reflexing: Apical margin
Mature Leaves:
   Margin:
      Incision depth (deepest penetration of the margin): Moderate
      Indentation (finest divisions of the margin): Crenate
      Undulation of apical margin: Moderate
   Green color: Munsell 5GY 5/4 (Medium green)
   Anthocyanin distribution: Absent
   Glossiness: Dull
   Blistering: Moderate
   Thickness: Intermediate
   Trichomes: Absent (smooth)
Plant
   Weight: 934.7 g
   Spread of frame leaves: 56 cm
   Head diameter (market trimmed with single cap leaf): 14.7 cm
   Head shape: Spherical
   Head size class: Large
   Head firmness: Firm
Butt:
   Shape: Rounded
   Midrib: Moderately raised
Core:
   Diameter at base of head: 36.5 mm
   Ratio of head diameter/core diameter: 4
   Height from base of head to apex: 41.2 mm
Bolting:
   Number of days from first water to seed stalk emergence under summer conditions: 72
   Bolting class: Medium
   Mature seed stalk height: 105.3 cm
   Mature seed stalk spread: 41.5 cm
   Bolter leaves: Curved
   Margin: Dentate
   Bolter habit:
      Terminal inflorescence: Present
      Lateral shoots: Present
      Basal side shoots: Absent
Disease Resistance:
   Lettuce Big-Vein Virus (LBVV): Susceptible
   Lettuce Mosaic Virus (LMV) strain Ls-1: Susceptible
   Powdery Mildew: Susceptible
   Corky Root Rot: Susceptible
   Downy Mildew (*Bremia lactucae*) (B1): Susceptible
   *Fusarium* Wilt (*Fusarium oxysporum* f. sp. *lactucae*) race 1: Resistant
Pest Resistance:
   *Nasonovia ribisnigri* biotype 0 (Nr: 0): Susceptible
Stress Resistance:
   Tipburn: Moderately resistant
   Heat: Susceptible
   Cold: Susceptible
   Pink rib: Susceptible
   Rusty brown discoloration: Susceptible
   Internal rib necrosis: Susceptible Comparisons to Other Lettuce Variety Table 13 below compares characteristics of lettuce variety 'PS 1525' with the lettuce variety 'Uppercut' (U.S. Patent Publication No. US 2021/0084853 A1). Column 1 lists the characteristics, column 2 shows the characteristics for lettuce variety 'PS 1525', and column 3 shows the characteristics for lettuce variety 'Uppercut'.

TABLE 13

| Characteristic | 'PS 1525' | 'Uppercut' |
| --- | --- | --- |
| Weight | 934.7 g | 893.2 g |
| Green color of mature leaves | Munsell 5GY 5/4 | Munsell 5GY 5/6 |
| Spread of frame leaves | 56 cm | 58.4 cm |
| Head diameter | 14.7 cm | 14.3 cm |
| Core diameter at base of head | 36.5 mm | 35.9 mm |
| Core height from base of head to apex | 41.2 mm | 38.9 mm |
| Mature seed stalk height | 105.3 cm | 111.1 cm |
| Mature seed stalk spread | 41.5 cm | 39.8 cm |

Table 14 below compares characteristics of lettuce variety 'PS 1525' with the lettuce variety 'Headmaster' (U.S. Plant Variety Protection Certificate No. 9800023). Column 1 lists the characteristics, column 2 shows the characteristics for lettuce variety 'PS 1525', and column 3 shows the characteristics for lettuce variety 'Headmaster'.

TABLE 14

| Characteristic | 'PS 1525' | 'Headmaster' |
| --- | --- | --- |
| Weight | 934.7 g | 702.4 g |
| Green color of mature leaves | Munsell 5GY 5/4 | Munsell 5GY 5/6 |
| Spread of frame leaves | 56 cm | 58.2 cm |
| Head diameter | 14.7 cm | 14.2 cm |
| Core diameter at base of head | 36.5 mm | 33.6 mm |
| Core height from base of head to apex | 41.2 mm | 30.2 mm |
| Mature seed stalk height | 105.3 cm | 106.2 cm |
| Mature seed stalk spread | 41.5 cm | 36.2 cm |

Tables 15A-15C below show results of a first trial that compares the head weight, head diameter, core length, core diameter, and frame diameter of 20 plants of the lettuce variety 'PS 1525' (Table 15A) with those of 20 plants of lettuce variety 'Uppercut' (Table 15B; U.S. Patent Publication No. US 2021/0084853 A1) and 20 plants of lettuce variety 'Headmaster' (Table 15C; U.S. Plant Variety Protection Certificate No. 9800023). The head weights shown are total head weights.

TABLE 15A

| 'PS 1525' | Head Wt. | Head Diameter | Core Length | Core Diameter | Frame Diameter |
|---|---|---|---|---|---|
| Max | 1250 g | 160 mm | 55 mm | 41 mm | 53.5 cm |
| Min | 960 g | 130 mm | 34 mm | 30 mm | 47.1 cm |
| Average | 1060.25 g | 146.75 mm | 42.15 mm | 36.4 mm | 50.57 cm |
| Std. Dev. | 83.88 | 9.06 | 5.10 | 3.45 | 1.61 |

TABLE 15B

| 'Uppercut' | Head Wt. | Head Diameter | Core Length | Core Diameter | Frame Diameter |
|---|---|---|---|---|---|
| Max | 1110 g | 151 mm | 45 mm | 40 mm | 58.3 cm |
| Min | 540 g | 120 mm | 22 mm | 25 mm | 50.4 cm |
| Average | 859.5 g | 136.5 mm | 35.4 mm | 33.1 mm | 52.815 cm |
| Std. Dev. | 152.98 | 7.74 | 5.72 | 3.46 | 2.18 |

TABLE 15C

| 'Headmaster' | Head Wt. | Head Diameter | Core Length | Core Diameter | Frame Diameter |
|---|---|---|---|---|---|
| Max | 890 g | 156 mm | 43 mm | 36 mm | 57.4 cm |
| Min | 620 g | 125 mm | 20 mm | 28 mm | 50.5 cm |
| Average | 759.75 g | 139.75 mm | 28.9 mm | 31.8 mm | 53.93 cm |
| Std. Dev. | 74.40 | 7.79 | 4.89 | 2.21 | 2.13 |

Tables 16A-16C below show results of a second trial that compares the head weight, head diameter, core length, core diameter, and frame diameter of 20 plants of the lettuce variety 'PS 1525' (Table 16A) with those of 20 plants of lettuce variety 'Uppercut' (Table 16B; U.S. Patent Publication No. US 2021/0084853 A1) and 20 plants of lettuce variety 'Headmaster' (Table 16C; U.S. Plant Variety Protection Certificate No. 9800023). The head weights shown are total head weights.

TABLE 16A

| 'PS 1525' | Head Wt. | Head Diameter | Core Length | Core Diameter | Frame Diameter |
|---|---|---|---|---|---|
| Max | 1110 g | 163 mm | 50 mm | 41 mm | 50.2 cm |
| Min | 775 g | 138 mm | 29 mm | 34 mm | 45.1 cm |
| Average | 955.75 g | 152.3 mm | 37.25 mm | 36.95 mm | 46.795 cm |
| Std. Dev. | 96.92 | 6.33 | 6.09 | 2.56 | 1.30 |

TABLE 16B

| 'Uppercut' | Head Wt. | Head Diameter | Core Length | Core Diameter | Frame Diameter |
|---|---|---|---|---|---|
| Max | 1140 g | 164 mm | 51 mm | 43 mm | 49.8 cm |
| Min | 740 g | 134 mm | 29 mm | 34 mm | 44.1 cm |
| Average | 977.5 g | 149.2 mm | 36.55 mm | 38.15 mm | 46.69 cm |
| Std. Dev. | 89.20 | 8.16 | 5.88 | 2.81 | 1.56 |

TABLE 16C

| 'Headmaster' | Head Wt. | Head Diameter | Core Length | Core Diameter | Frame Diameter |
|---|---|---|---|---|---|
| Max | 1000 g | 165 mm | 40 mm | 44 mm | 49.1 cm |
| Min | 635 g | 133 mm | 20 mm | 29 mm | 42.1 cm |
| Average | 799.5 g | 149.15 mm | 30.2 mm | 37.55 mm | 44.99 cm |
| Std. Dev. | 93.51 | 8.90 | 5.93 | 3.61 | 1.72 |

Tables 17A-17C below show results of a third trial that compares the head weight, head diameter, core length, core diameter, and frame diameter of 20 plants of the lettuce variety 'PS 1525' (Table 17A) with those of 20 plants of lettuce variety 'Uppercut' (Table 17B; U.S. Patent Publication No. US 2021/0084853 A1) and 20 plants of lettuce variety 'Headmaster' (Table 17C; U.S. Plant Variety Protection Certificate No. 9800023). The head weights shown are total head weights.

TABLE 17A

| 'PS 1525' | Head Wt. | Head Diameter | Core Length | Core Diameter | Frame Diameter |
|---|---|---|---|---|---|
| Max | 1130 g | 159 mm | 73 mm | 45 mm | 56.1 cm |
| Min | 630 g | 133 mm | 36 mm | 31 mm | 47.4 cm |
| Average | 938.25 g | 148.5 mm | 57.35 mm | 40.25 mm | 51.565 cm |
| Std. Dev. | 147.31 | 7.03 | 9.29 | 3.26 | 2.03 |

TABLE 17B

| 'Uppercut' | Head Wt. | Head Diameter | Core Length | Core Diameter | Frame Diameter |
|---|---|---|---|---|---|
| Max | 1140 g | 164 mm | 65 mm | 44 mm | 59.1 cm |
| Min | 740 g | 138 mm | 41 mm | 32 mm | 47.3 cm |
| Average | 994.25 g | 149.35 mm | 52 mm | 39.15 mm | 52.09 cm |
| Std. Dev. | 114.46 | 7.85 | 7.42 | 3.10 | 3.37 |

TABLE 17C

| 'Headmaster' | Head Wt. | Head Diameter | Core Length | Core Diameter | Frame Diameter |
|---|---|---|---|---|---|
| Max | 900 g | 164 mm | 62 mm | 40 mm | 57.1 cm |
| Min | 485 g | 125 mm | 30 mm | 32 mm | 46.5 cm |
| Average | 689.25 g | 144.55 mm | 40.05 mm | 35.6 mm | 51.195 cm |
| Std. Dev. | 100.53 | 12.72 | 7.62 | 2.16 | 2.20 |

Tables 18A-18C below show results of a fourth trial that compares the head weight, head diameter, core length, core diameter, and frame diameter of 20 plants of the lettuce variety 'PS 1525' (Table 18A) with those of 20 plants of lettuce variety 'Uppercut' (Table 18B; U.S. Patent Publication No. US 2021/0084853 A1) and 20 plants of lettuce variety 'Headmaster' (Table 18C; U.S. Plant Variety Protection Certificate No. 9800023). The head weights shown are total head weights.

TABLE 18A

| 'PS 1525' | Head Wt. | Head Diameter | Core Length | Core Diameter | Frame Diameter |
|---|---|---|---|---|---|
| Max | 997 g | 159 mm | 36 mm | 40 mm | 86 cm |
| Min | 453 g | 123 mm | 20 mm | 28 mm | 68 cm |
| Average | 784.35 g | 139.8 mm | 27.9 mm | 32.3 mm | 75.125 cm |
| Std. Dev. | 129.30 | 11.20 | 4.04 | 2.89 | 4.59 |

TABLE 18B

| 'Uppercut' | Head Wt. | Head Diameter | Core Length | Core Diameter | Frame Diameter |
|---|---|---|---|---|---|
| Max | 710 g | 163 mm | 45 mm | 41 mm | 93.5 cm |
| Min | 420 g | 111 mm | 2 mm | 25 mm | 72 cm |

TABLE 18B-continued

| 'Upper-cut' | Head Wt. | Head Diameter | Core Length | Core Diameter | Frame Diameter |
|---|---|---|---|---|---|
| Average | 741.5 g | 137.4 mm | 31.5 mm | 33.35 mm | 81.875 cm |
| Std. Dev. | 121.11 | 13.14 | 10.40 | 3.70 | 7.48 |

TABLE 18C

| 'Head-master' | Head Wt. | Head Diameter | Core Length | Core Diameter | Frame Diameter |
|---|---|---|---|---|---|
| Max | 865 g | 148 mm | 34 mm | 40 mm | 99 cm |
| Min | 400 g | 120 mm | 10 mm | 20 mm | 70.5 cm |
| Average | 561.25 g | 136.25 mm | 21.8 mm | 29.6 mm | 82.525 cm |
| Std. Dev. | 178.10 | 6.71 | 6.68 | 5.21 | 8.59 |

Figure 5A:
FIGS. 5A-5S show comparisons between lettuce varieties 'PS 1525', 'Uppercut' (U.S. Patent Publication No. US 2021/0084853 A1), and 'Headmaster' (U.S. Plant Variety Protection Certificate No. 9800023).
Figure 5B:
FIG. 5B shows plants of lettuce varieties 'PS 1525' (top) and 'Headmaster' (bottom).
Figure 5C:
FIG. 5C shows a bottom view of heads of lettuce varieties 'PS 1525' (top) and 'Uppercut' (bottom).
Figure 5D:
FIG. 5D shows a bottom view of heads of lettuce varieties 'PS 1525' (top) and 'Headmaster' (bottom).
Figure 5E:
FIG. 5E shows a side view of heads of lettuce varieties 'PS 1525' (top) and 'Uppercut' (bottom).
Figure 5F:
FIG. 5F shows a side view of heads of lettuce varieties 'PS 1525' (top) and 'Headmaster' (bottom).
Figure 5G:
FIG. 5G shows a top view of heads of lettuce varieties 'PS 1525' (top) and 'Uppercut' (bottom).
Figure 5H:
FIG. 5H shows a top view of heads of lettuce varieties 'PS 1525' (top) and 'Headmaster' (bottom).
Figure 5I:
FIG. 5I shows a cross-sectional view of heads of lettuce varieties 'PS 1525' (top) and 'Uppercut' (bottom).
Figure 5J:
FIG. 5J shows a cross-sectional view of heads of lettuce varieties 'PS 1525' (top) and 'Headmaster' (bottom).
Figure 5K:
FIG. 5K shows a bottom view of heads of lettuce variety 'PS 1525'.
Figure 5L:
FIG. 5L shows a bottom view of heads of lettuce variety 'Uppercut'.
Figure 5M:
FIG. 5M shows a bottom view of heads of lettuce variety 'Headmaster'.
Figure 5N:
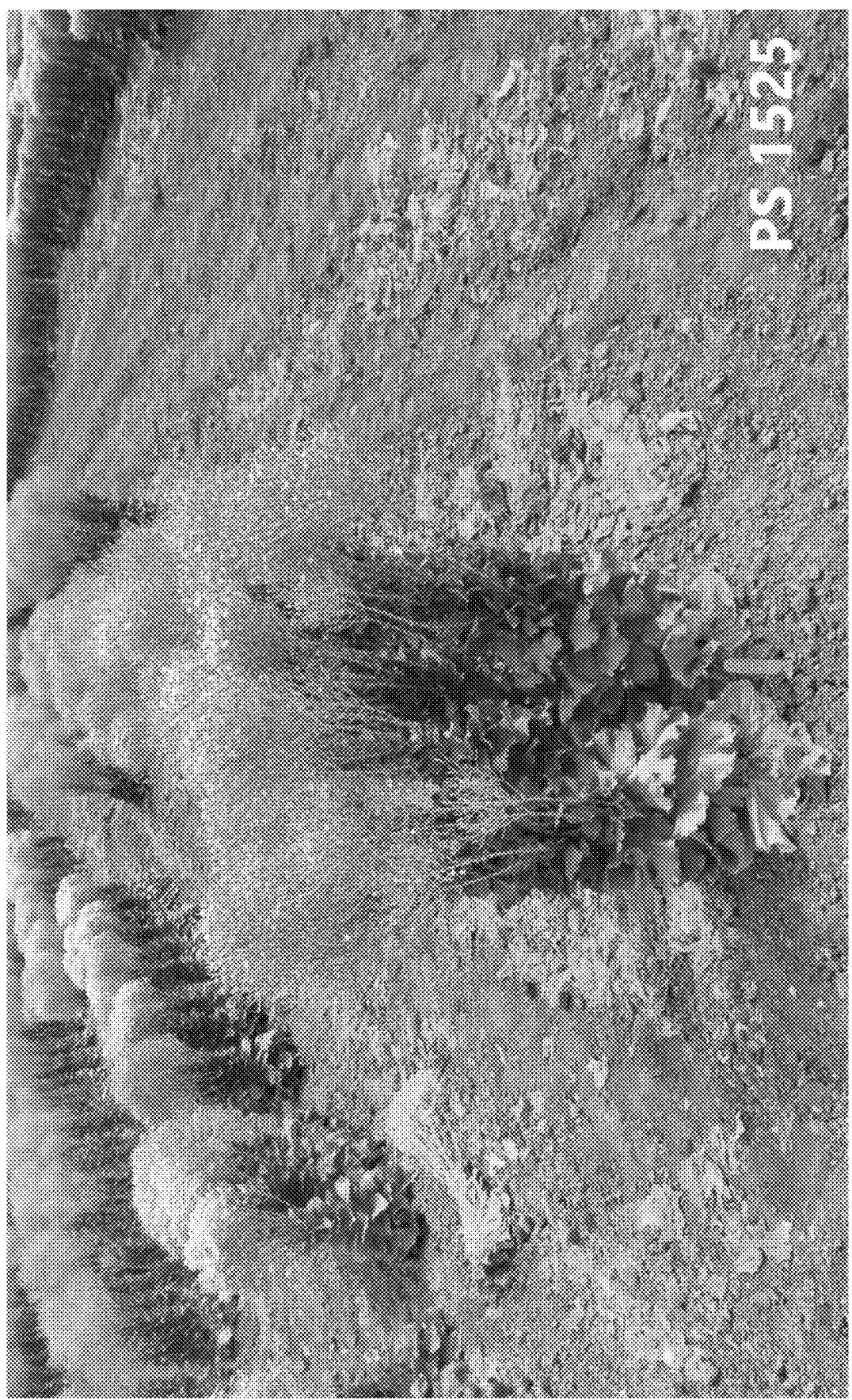
FIG. 5N shows bolting plants of lettuce variety 'PS 1525'.
Figure 50:
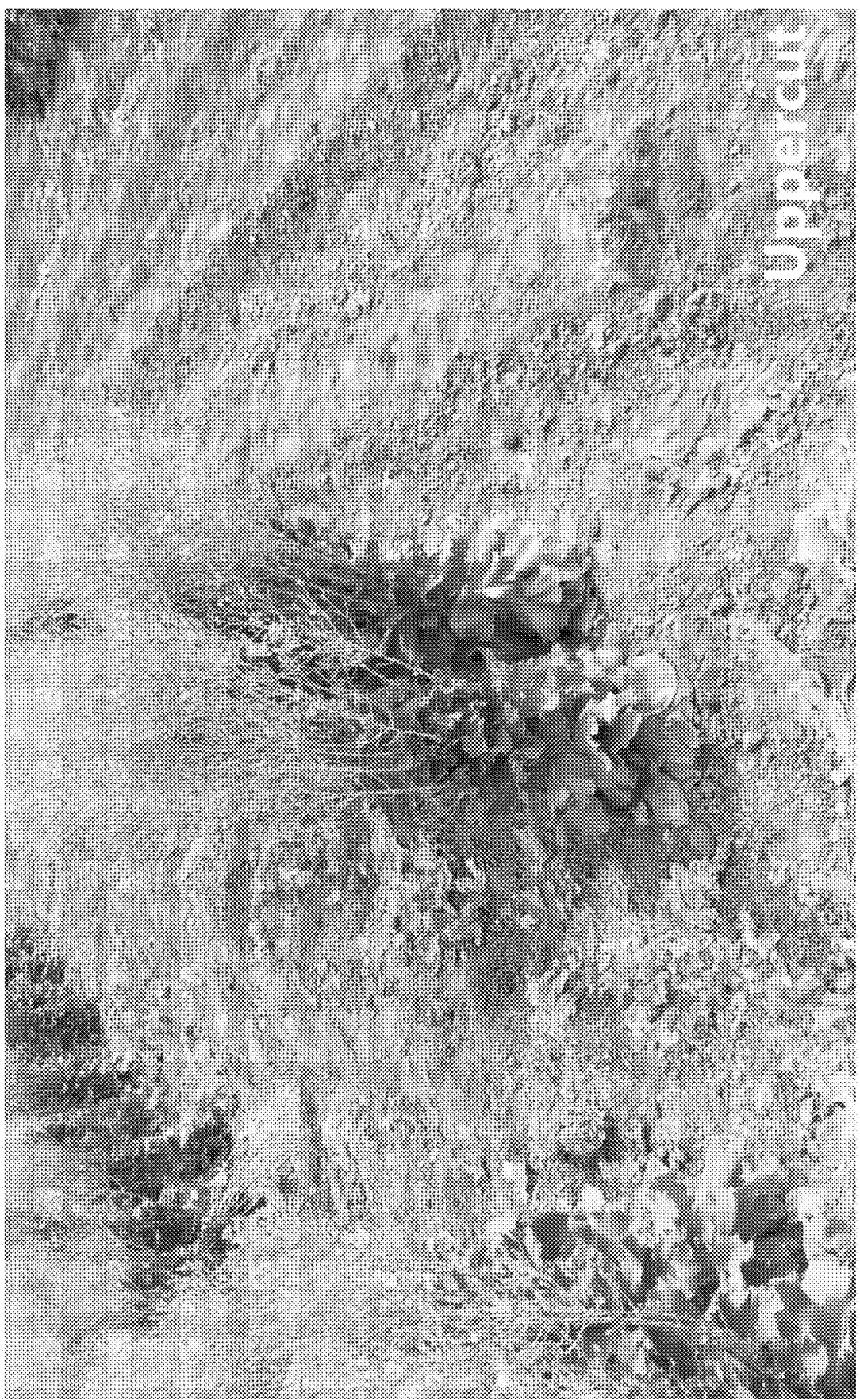
Figure 5P:
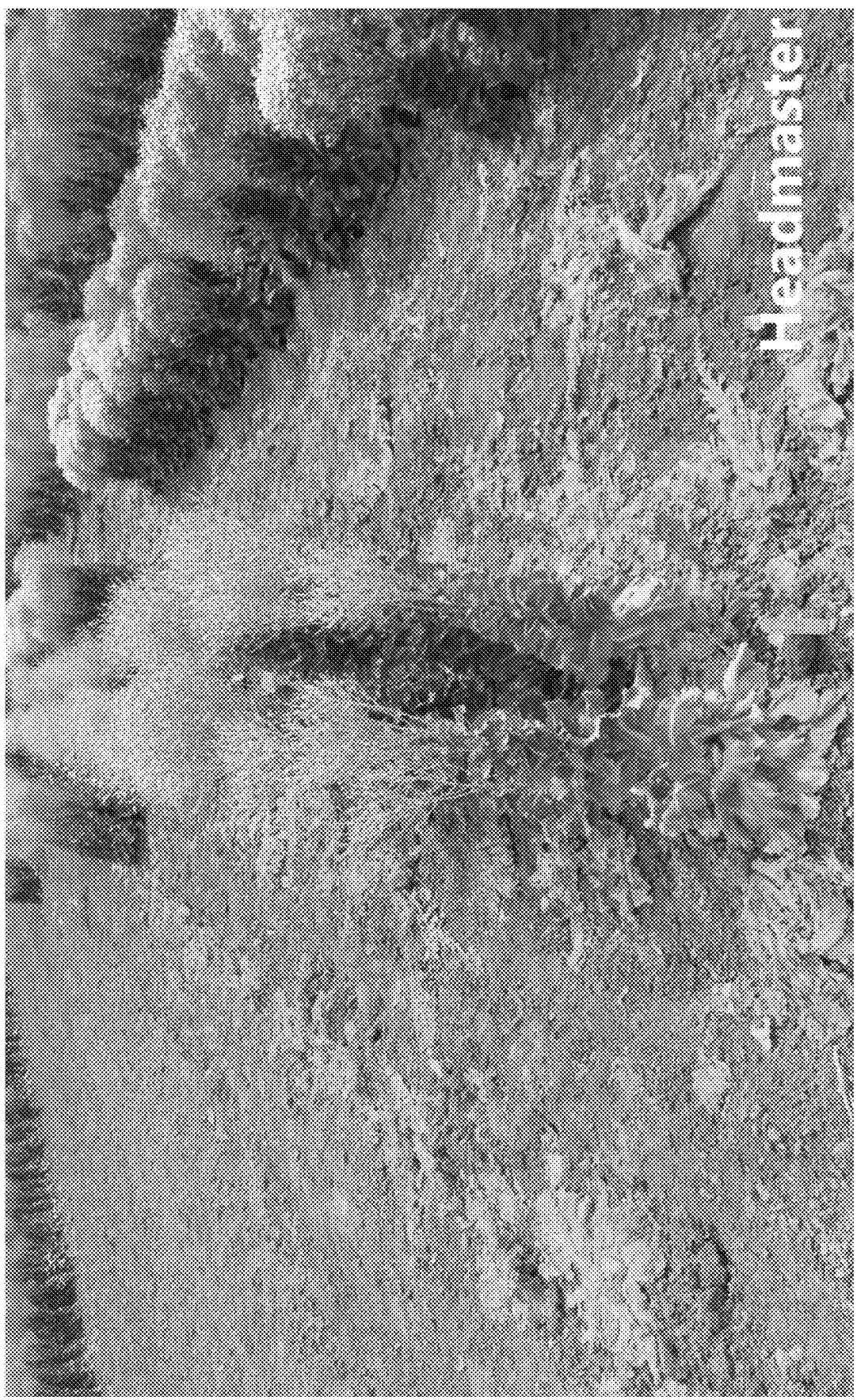
FIG. 5P shows bolting plants of lettuce variety 'Headmaster'.
Figure 5Q:
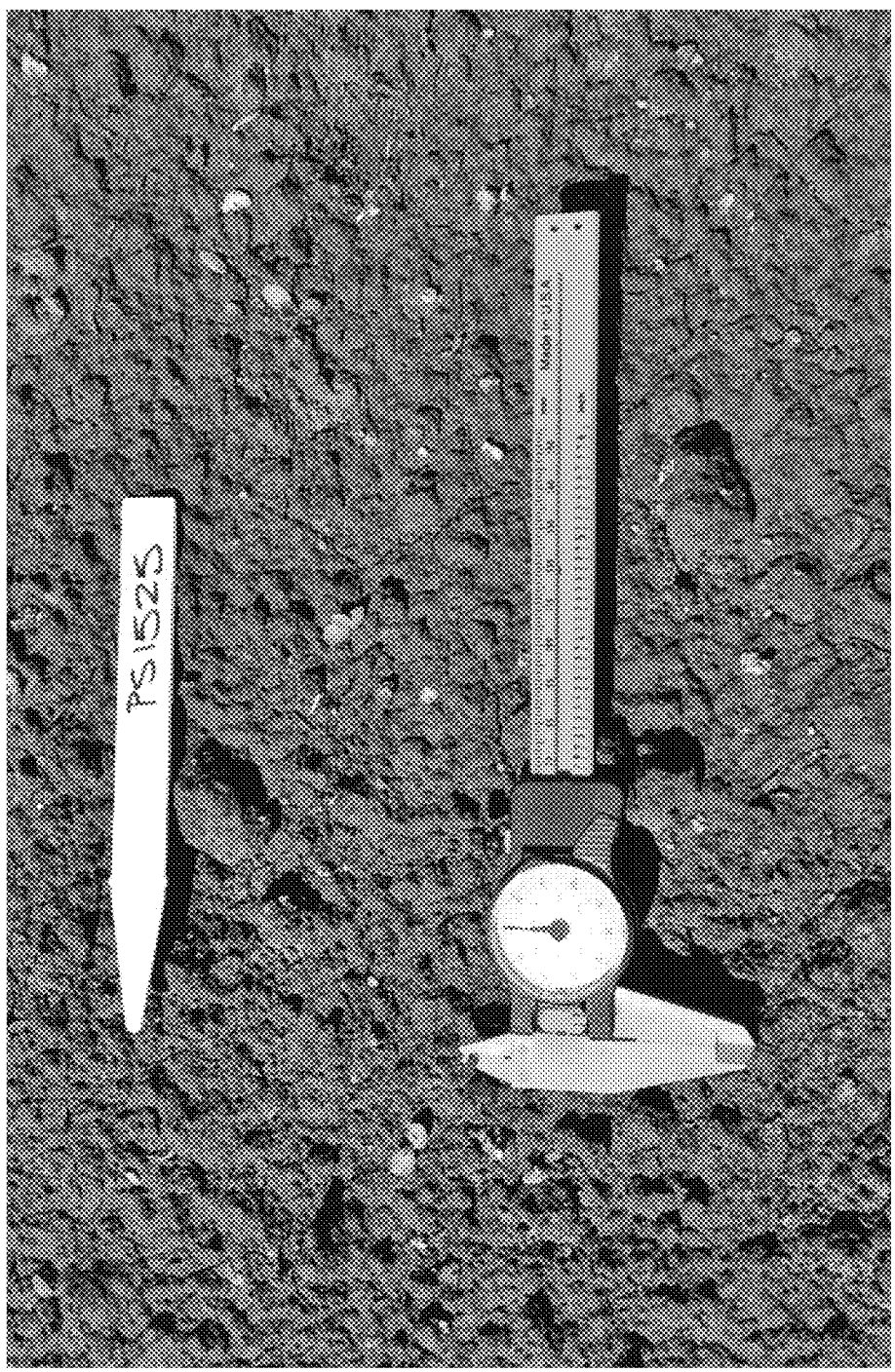
FIG. 5Q shows seedlings of lettuce variety 'PS 1525'. FIG.
Figure 5R:
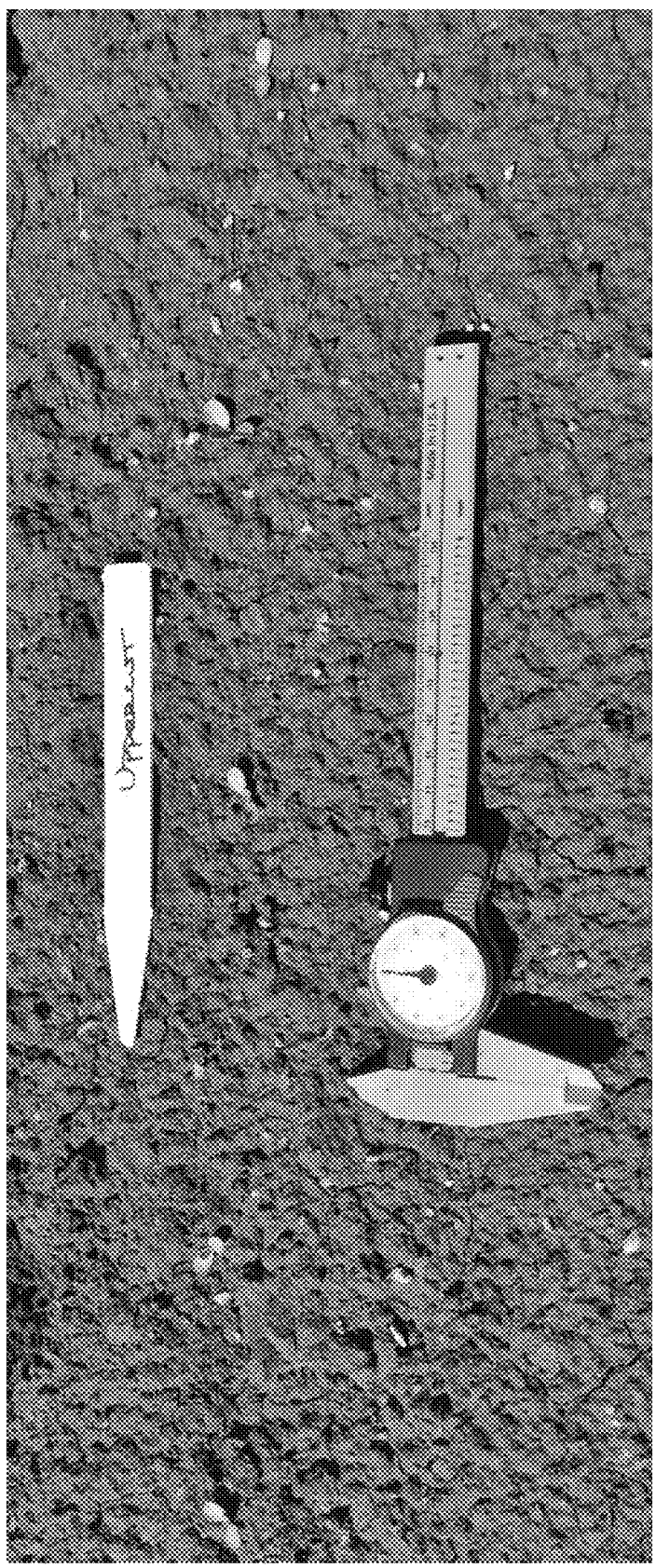
FIG. 5O shows bolting plants of lettuce variety 'Uppercut'.
Figure 5S:
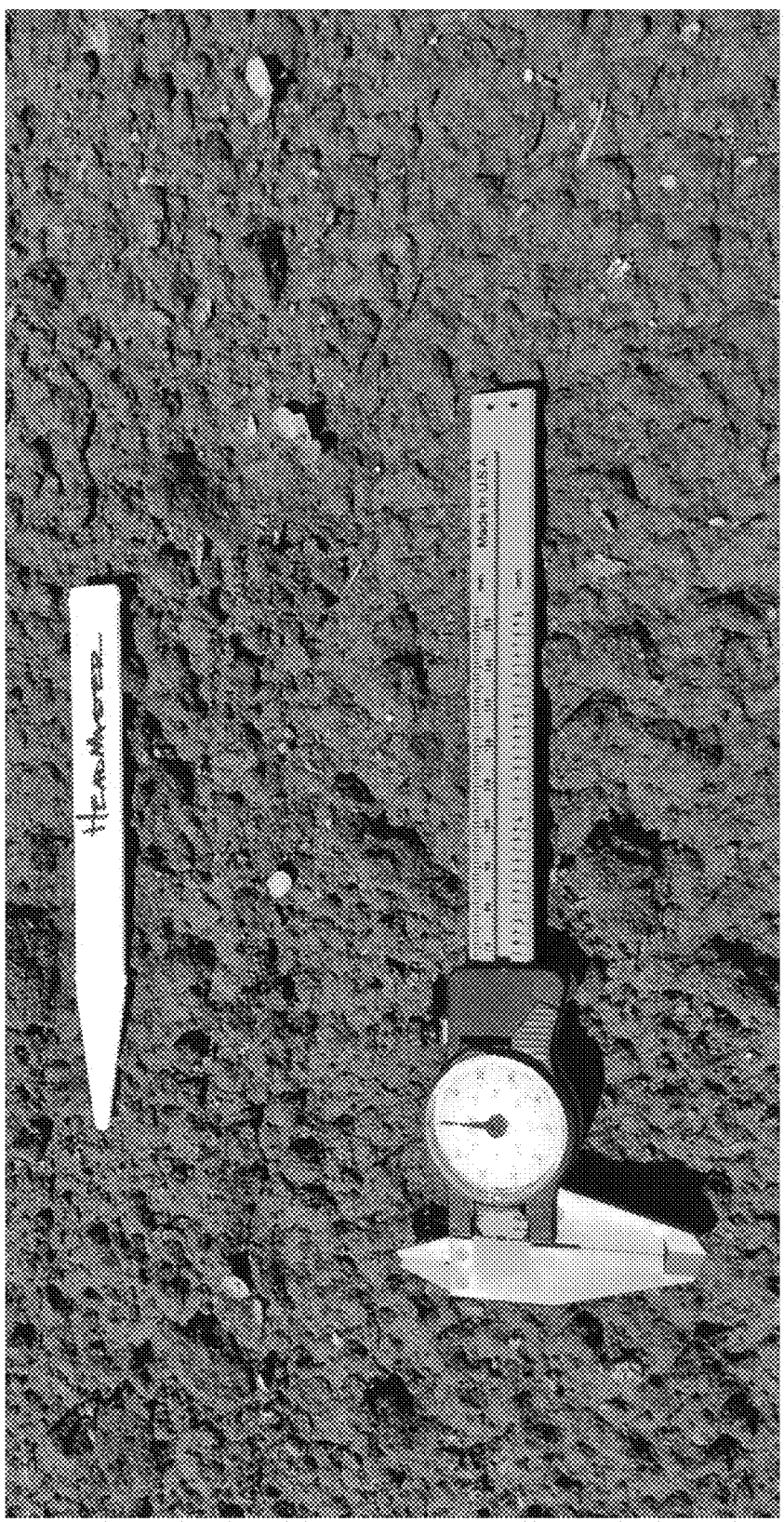

Further distinguishing features are apparent from the comparison of the variety 'PS 1525' with the varieties 'Uppercut' and 'Headmaster' depicted in FIGS. 5A-5S.

Further Embodiments

Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma, Arizona and the Salinas Valley, California.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possibilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27 (8): 907-908 both of which are hereby incorporated by reference in their entirety for the purpose of providing details on the techniques well known in the art.

Selection

In addition to crossing, selection may be used to identify and isolate new lettuce lines. In lettuce selection, lettuce seeds are planted, the plants are grown and single plant selections are made of plants with desired characteristics. Such characteristics may include improved head, heart, and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

Lettuce Variety 'PS 1525'

A deposit of the lettuce variety 'PS 1525' is maintained by Pinnacle Seed, Inc., having an address of P.O. Box 222672, Carmel, California 93923, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Virginia, 20110, USA.

The lettuce variety 'PS 1525' was deposited on May 3, 2024 according to the Budapest Treaty in the American Type Culture Collection (ATCC), ATCC Patent Depository, 10801 University Boulevard, Manassas, Virginia, 20110, USA. The deposit has been assigned ATCC number PTA-127758. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

What is claimed:

1. A *Lactuca sativa* seed designated as 'PS 1525', representative sample of seed having been deposited under ATCC Accession Number PTA-127758.

2. A *Lactuca sativa* plant produced by growing the seed of claim 1.

3. A plant part from the plant of claim 2.

4. The plant part of claim 3, wherein said part is a head, a heart, a leaf, or a portion thereof.

5. The plant part of claim 4, wherein said part is a head or a heart.

6. A *Lactuca sativa* plant having all the physiological and morphological characteristics of the *Lactuca sativa* plant of claim 2.

7. A plant part from the plant of claim 6.

8. The plant part of claim 7, wherein said part is a head, a heart, a leaf, or a portion thereof.

9. The plant part of claim 8, wherein said part is a head or a heart.

10. An $F_1$ hybrid *Lactuca sativa* plant having 'PS 1525' as a parent where 'PS 1525' is grown from the seed of claim 1.

11. A pollen grain or an ovule of the plant of claim 2.

12. A tissue culture of the plant of claim 2.

13. A *Lactuca sativa* plant regenerated from the tissue culture of claim 12, wherein the plant has all of the morphological and physiological characteristics of a lettuce plant produced by growing seed designated as 'PS 1525', representative sample of seed having been deposited under ATCC Accession Number PTA-127758.

14. A method of making *Lactuca sativa* seeds, said method comprising crossing the plant of claim 2 with another lettuce plant and harvesting seed therefrom.

15. A method of selecting *Lactuca sativa*, comprising:
 a) growing more than one plant from the seed of claim 1; and
 b) selecting a plant from step a).

* * * * *